(12) United States Patent
Zhuang et al.

(10) Patent No.: US 11,071,624 B2
(45) Date of Patent: Jul. 27, 2021

(54) ARTIFICIAL HEART VALVE STENT, ARTIFICIAL HEART VALVE AND IMPLANTATION METHOD

(71) Applicant: LIFETECH SCIENTIFIC (SHENZHEN) CO., LTD, Shenzhen (CN)

(72) Inventors: Jian Zhuang, Shenzhen (CN); Huiming Guo, Shenzhen (CN); Huanlei Huang, Shenzhen (CN); Zhiwei Wang, Shenzhen (CN); Xiangdong Liu, Shenzhen (CN); Mingjuan Fu, Shenzhen (CN); Wei Jiang, Shenzhen (CN); Deyuan Zhang, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 184 days.

(21) Appl. No.: 15/781,944

(22) PCT Filed: Mar. 18, 2016

(86) PCT No.: PCT/CN2016/076778
§ 371 (c)(1),
(2) Date: Jun. 6, 2018

(87) PCT Pub. No.: WO2017/101232
PCT Pub. Date: Jun. 22, 2017

(65) Prior Publication Data
US 2018/0360600 A1    Dec. 20, 2018

(30) Foreign Application Priority Data
Dec. 15, 2015  (CN) .......................... 201510936869.1

(51) Int. Cl.
*A61F 2/24* (2006.01)
*A61B 17/00* (2006.01)
(Continued)

(52) U.S. Cl.
CPC ........ *A61F 2/2418* (2013.01); *A61B 17/0469* (2013.01); *A61B 17/06* (2013.01);
(Continued)

(58) Field of Classification Search
CPC .... A61F 2/2409; A61F 2/2412; A61F 2/2418; A61F 2/2436
See application file for complete search history.

(56) References Cited

U.S. PATENT DOCUMENTS

| 9,681,948 B2* | 6/2017 | Levi .................. A61B 17/0057 |
| 2012/0022639 A1* | 1/2012 | Hacohen .............. A61F 2/2439 623/2.11 |

(Continued)

FOREIGN PATENT DOCUMENTS

| CN | 103079498 A | 5/2013 |
| CN | 103997990 A | 8/2014 |
| WO | 2015/188066 A1 | 12/2015 |

OTHER PUBLICATIONS

International Search Report dated Aug. 29, 2016 of corresponding International Application No. PCT/CN2016/076778; 8 pgs.

*Primary Examiner* — Katrina M Stransky
*Assistant Examiner* — Mohammed S Adam
(74) *Attorney, Agent, or Firm* — Maier & Maier, PLLC

(57) ABSTRACT

An artificial heart valve stent including: a tubular stent body having an inflow side end and an outflow side end, the inflow side end and the outflow side end being opposite to each other; an inflow side skirt surrounding the external wall of the stent body; and an outflow side skirt surrounding the external wall of the stent body. In a spread state, free ends
(Continued)

of the inflow side skirt and the outflow side skirt extend toward the inflow side end; and the inflow side skirt cooperates with the outflow side skirt to clamp heart valve tissues. The artificial heart valve stent can be steadily arranged on heart valve tissues, prolong the service life of an artificial heart valve and reduce the risk of another artificial heart valve replacement for the patient.

19 Claims, 19 Drawing Sheets

(51) Int. Cl.
*A61B 17/34* (2006.01)
*A61B 18/14* (2006.01)
*A61B 17/04* (2006.01)
*A61B 17/06* (2006.01)
*A61B 18/00* (2006.01)
*A61B 90/00* (2016.01)

(52) U.S. Cl.
CPC ...... *A61B 17/3478* (2013.01); *A61B 18/1477* (2013.01); *A61B 2017/00247* (2013.01); *A61B 2017/00575* (2013.01); *A61B 2017/00606* (2013.01); *A61B 2017/00623* (2013.01); *A61B 2017/00663* (2013.01); *A61B 2018/00351* (2013.01); *A61B 2018/00601* (2013.01); *A61B 2090/061* (2016.02); *A61F 2/2436* (2013.01); *A61F 2220/0008* (2013.01); *A61F 2220/0025* (2013.01); *A61F 2220/0058* (2013.01); *A61F 2250/0039* (2013.01)

(56) References Cited

U.S. PATENT DOCUMENTS

| | | | |
|---|---|---|---|
| 2012/0078353 A1 | 3/2012 | Quadri et al. | |
| 2014/0222136 A1 | 8/2014 | Geist et al. | |
| 2015/0196390 A1* | 7/2015 | Ma | A61F 2/2418 623/2.17 |
| 2016/0113764 A1* | 4/2016 | Sheahan | A61F 2/2418 623/2.17 |
| 2016/0158000 A1* | 6/2016 | Granada | A61F 2/2418 623/2.18 |

* cited by examiner

ARTIFICIAL HEART VALVE STENT, ARTIFICIAL HEART VALVE AND IMPLANTATION METHOD

FIELD

The present application relates to the field of interventional medical devices, and more particularly relates to an artificial heart valve stent, an artificial heart valve having the artificial heart valve stent, and an implantation method of the artificial heart valve.

BACKGROUND

Heart valves grow between atriums and ventricles as well as between the ventricles and the main artery, and may achieve effects of one-way valves and assist blood in one-way movement. Four valves of human body are respectively called a mitral valve, a tricuspid valve, an aortic valve and a pulmonary valve. The pathological change of these valves will affect the movement of the blood, which leads to a heart function abnormity, thus finally causing a heart failure.

A valve pathological change generally includes stenosis or insufficiency. The stenosis is that the opening degree of a valve is not enough, which causes reduction of blood entering the next cardiac chamber, and the insufficiency is that the valve is closed insufficiently, which causes backflow of part of the blood. Once the stenosis and/or the insufficiency occurs, it will obstruct normal blood flow and increase corresponding heart burden, thus leading to lesion to the normal functions of the heart, which results in the heart failure and change of functions of multiple organs of the body.

At the present, there are two main surgical therapies for heart valve diseases: (1) valvuloplasty for repairing a diseased valve, and (2) valve replacement for replacing the diseased valve with an artificial mechanical valve or a biological valve.

The valvuloplasty is generally applied to a minimal pathological change of mitral valve or tricuspid valve, and the valve replacement is mostly applied to severe pathological change of heart valve, particularly severe pathological change of rheumatic heart valve. Main therapies of the valvuloplasty include Key's plasty, DeVega plasty, plasty by using a C-shaped annulus, and the like. In the valve replacement, an artificial valve is used to replace a human diseased heart valve, such as the mechanical valve and the biological valve. The mechanical valve has a long life, but a patient needs to take medication to resist coagulation for the remainder of their life, which commonly causes complications. The biological valve does not need lifelong coagulation resistance, but it has a short life.

In recent years, for patients suffering from cuspid valve stenosis and backflow, percutaneous and via-sheath cuspid valve replacement may be also adopted, namely this operation is carried out via intervention and minimally invasive surgery to avoid the pain caused by thoracotomy of the patients.

A right heart system of a human heart (as shown in prior art FIG. 1) includes a right atrium 3 and a right ventricle 5. A left heart system of the human heart includes a left atrium 4, a left ventricle 6, and a mitral annulus 8, a mitral anterior valve leaflet 15, a mitral posterior valve leaflet 12 and a chordae tendineae 16 which are located between the left atrium 4 and the left ventricle 6. An artificial valve device in the prior art includes an anterior valve leaflet anchoring member and a posterior valve leaflet anchoring member. The anterior valve leaflet anchoring member and the posterior valve leaflet anchoring member are respectively fixed on the mitral anterior valve leaflet 15 and the mitral posterior valve leaflet 12 to prevent the artificial valve device from falling off into the left atrium 4 under the impact of the blood flow. As valve leaflet tissues are vulnerable, the anterior valve leaflet anchoring member 4 and the posterior valve leaflet anchoring member 3 may easily damage the valve leaflets and easily fall off from the valve leaflets, thereby directly leading to low stability of an artificial heart valve on heart valve tissues, affecting the service life of the artificial heart valve, and increasing the risk of another valve replacement for the patient.

SUMMARY

In view of this, it is necessary to provide an artificial heart valve stent, an artificial heart valve having the artificial heart valve stent, and an implantation method of the artificial heart valve. The artificial heart valve stent may be steadily arranged on heart valve tissues, may prolong the service life of the artificial heart valve, and may reduce the risk of another valve replacement for a patient.

The present application provides an artificial heart valve stent, including a tubular stent body having an inflow side end and an outflow side end opposite to the inflow side, an inflow side skirt surrounding the external wall of the stent body, and an outflow side skirt surrounding the external wall of the stent body. In a released state, the free ends of both the inflow side skirt and the outflow side skirt extend towards the inflow side end; and the inflow side skirt is used for cooperating with the outflow side skirt to clamp heart valve tissues.

In one embodiment, the artificial heart valve stent further includes a tubular connection stent surrounding the external wall of the stent body, and the inflow side skirt and the outflow side skirt are located at two ends of the tubular connection stent respectively.

In one embodiment, the tubular connection stent and the stent body are independently formed, and then are fixedly connected into a whole.

In one embodiment, a projection of the end, which is connected with the tubular stent body, of the inflow side skirt on a section parallel to the longitudinal central axial line of the tubular stent body is separated from a projection of the inflow side end on the section parallel to the longitudinal central axial line of the tubular stent body.

In one embodiment, the distance between the end, which is connected with the tubular stent body, of the inflow side skirt and the inflow side end is greater than or equal to the distance between the end, which is connected with the tubular stent body, of the outflow side skirt and the outflow side end.

In one embodiment, a projection of the end, which is connected with the tubular stent body, of the outflow side skirt on the section parallel to the longitudinal central axial line of the tubular stent body is separated from a projection of the outflow side end on the section parallel to the longitudinal central axial line of the tubular stent body.

In one embodiment, the inflow side skirt includes an inflow side clamping portion connected with the stent body, and an inflow side upwarping portion connected with the inflow side clamping portion; the inflow side clamping portion is located between the inflow side upwarping portion and the stent body; the end, which is away from the inflow side clamping portion, of the inflow side upwarping portion is the free end of the inflow side skirt; and an included angle is formed between the inflow side upwarping portion and the inflow side clamping portion.

In one embodiment, the inflow side upwarping portion includes an inflow side waveform structure surrounding the stent body.

In one embodiment, the outflow side skirt includes an outflow side clamping portion connected with the stent body, and an outflow side upwarping portion connected with the outflow side clamping portion; the outflow side clamping portion is located between the outflow side upwarping portion and the stent body; the end, which is away from the outflow side clamping portion, of the outflow side upwarping portion is the free end of the outflow side skirt; and an included angle is formed between the outflow side upwarping portion and the outflow side clamping portion.

In one embodiment, the inflow side skirt includes a plurality of mutually separated first skirt subunits, and each first skirt subunit is disposed on the stent body in a weaving manner.

In one embodiment, the valve stent further comprises a plurality of inflow side anchoring members are arranged on the inflow side skirt, and the free ends of the inflow side anchoring members on the inflow side skirt extend towards the side of the outflow side end.

In one embodiment, the distance between the end, which is connected with the tubular stent body, of the inflow side skirt and the end, which is connected with the tubular stent body, of the outflow side skirt ranges from 2 mm to 6 mm In one embodiment, the valve stent further comprises connection elements arranged on the free end of the inflow side skirt.

In one embodiment, the valve stent further comprises a flow resisting cloth covering at least one of the inflow side skirt and the outflow side skirt.

The present application further provides an artificial heart valve, including the above-mentioned artificial heart valve stent and valve leaflets, and the valve leaflets are arranged inside the tubular stent body.

The present application further provides an implantation method of an interventional medical device, including: forming a small incision in the right thorax to expose the atrium, delivering the above-mentioned artificial heart valve to an implantation position of a heart system through the small incision, and fixing the artificial heart valve on tissues of the heart system.

In one embodiment, the heart valve is an artificial mitral valve; after the step of forming the small incision in the right thorax to expose the atrium, and before the step of delivering the artificial heart valve to the implantation position of the heart system through the small incision, the implantation method further includes a step of delivering a guide wire to the left ventricle through the small incision.

In one embodiment, the step of delivering the guide wire to the left ventricle through the small incision includes: suturing a mattress type pocket on the atrial wall, delivering the needle tip of a puncture needle into the left atrium through the mattress type pocket, then delivering the distal end of the guide wire into the left atrium along an inner cavity of the puncture needle, and delivering the distal end into the left ventricle through the mitral valve.

In one embodiment, the step of delivering the guide wire to the left ventricle through the small incision includes: suturing a mattress type pocket on the right atrial wall, delivering the needle tip of a radio frequency punching needle into the left atrium through the mattress type pocket, the right atrium and the atrial septum, then delivering the distal end of the guide wire into the left atrium along an inner cavity of the radio frequency punching needle, and delivering the distal end into the left ventricle through the mitral valve.

In one embodiment, the step of delivering the guide wire to the left ventricle through the small incision includes: suturing a mattress type pocket around a pre-puncture position of the interatrial groove, delivering the needle tip of a puncture needle into the left atrium through the mattress type pocket, then delivering the distal end of the guide wire into the left atrium along an inner cavity of the puncture needle, and delivering the distal end into the left ventricle through the mitral valve.

Compared with the prior art, the artificial heart valve stent of the present application has the advantages that the inflow side skirt and the outflow side skirt cooperate with each other to clamp heart valve tissues, so that the artificial heart valve stent may be steadily arranged on the heart valve tissues, prolong the service life of the artificial heart valve having the artificial heart valve stent and reduce the risk of another valve replacement for a patient. Compared with the prior art, the implantation method of the present application at least has the following advantages: (1) in the surgical procedure of the present application, no extracorporeal circulation is needed, so that the harm of a large surgical trauma is avoided; (2) in the surgical procedure of the present application, puncturing is implemented via the small incision in the right thorax instead of a vascular path, so that the size of the interventional medical device is free of the limit of the size of a blood vessel, and the structural design of the interventional medical device is flexible; (3) in the surgical procedure of the present application, the puncturing is carried out via the right atrium which has the blood pressure less than that of the left ventricle and has a thinner muscular layer, so that no bleeding or a small bleeding amount is caused at a puncture point, and the puncturing is easy to carry out; (4) an interventional medical device recycling device of the present application is arranged in the left atrium to avoid incidence of left ventricular outflow tract obstruction and improve the surgical safety; and (5) in the surgical procedure of the present application, a delivery device for carrying the interventional medical device is relatively far from the chordae tendineae to prevent the delivery device or the interventional medical device from touching the chordae tendineae, thus reducing the incidence of a phenomenon that the chordae tendineae twines around the delivery device or the interventional medical device, and making the surgery safer.

BRIEF DESCRIPTION OF THE DRAWINGS

A further description will be made to the present application in combination with accompanying drawings and embodiments as follows. In the drawings:

FIG. 12 is a schematic diagram of a structure of the interventional medical device in

FIG. 2;

FIG. 13 is a schematic diagram of a stent of the interventional medical device in

FIG. 12;

FIG. 36 is a schematic diagram of the right atrium after the puncture needle in

FIG. 35 is removed;

DETAILED DESCRIPTION OF THE INVENTION

For the purpose of making the above objects, features and advantages of the present application more clear and understandable, a detailed description will be made to specific implementation modes of the present application in combination with drawings as follows. Many specific details are described in the description below to facilitate full understanding of the present application. However, the present application may be implemented in many other modes different from the description herein, and a person skilled in the art can make similar improvements without departing from the contents of the present application, so that the present application may not be limited by disclosed specific implantation modes below.

It should be noted that when an element is referred to as being "fixed" on another element, it may be directly on another element or a centered element may also exist. When one element is deemed as being "connected" with another element, it may be directly connected to another element or a centered element may possibly exist at the same time. In the field of intervention, generally, an end relatively close to an operator is called a proximal end, and an end relatively far away from the operator is called a distal end.

It also should be noted that an implantation method of an interventional medical device of the present application is described by taking an artificial heart valve implanted into a mitral valve as an example, and the implantation method of the present application may be further used to implant interventional medical devices such as a left atrial appendage occluder and an atrial septal defect occluder. It also should be noted that a heart valve tissue related herein is one or a combination of several of heart tissues such as a valve annulus, a valve leaflet, a chordae tendineae and a papillary muscle. In a delivery state, the artificial heart valve is retracted in a delivery device to facilitate delivery; and in a spread state, the artificial heart valve is separated from the delivery device, then expands in a radial direction, and is fitted and fixed with the heart tissues into a whole.

Unless otherwise defined, all technical and scientific terms used herein have the same meanings of general understandings of persons skilled in the art of the present application. Terms used in the description of the present application herein are only intended to describe the specific embodiments, but not to limit the present application. Terms "and/or" used herein include any and all combinations of one or multiple relevant listed items.

Figure 1:
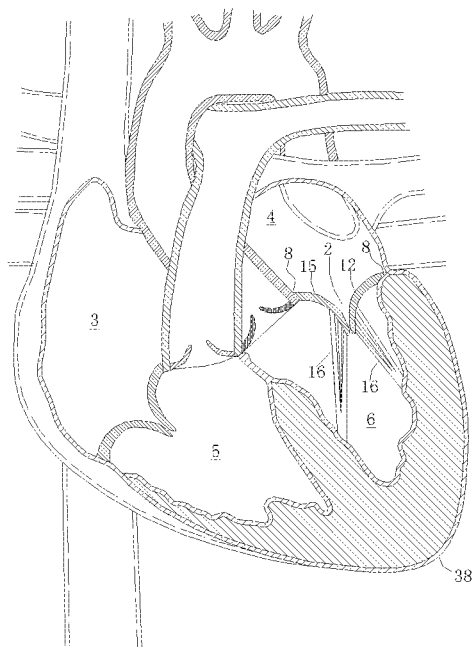
FIG. 1 is a schematic diagram of a human heart system.
Figure 2:
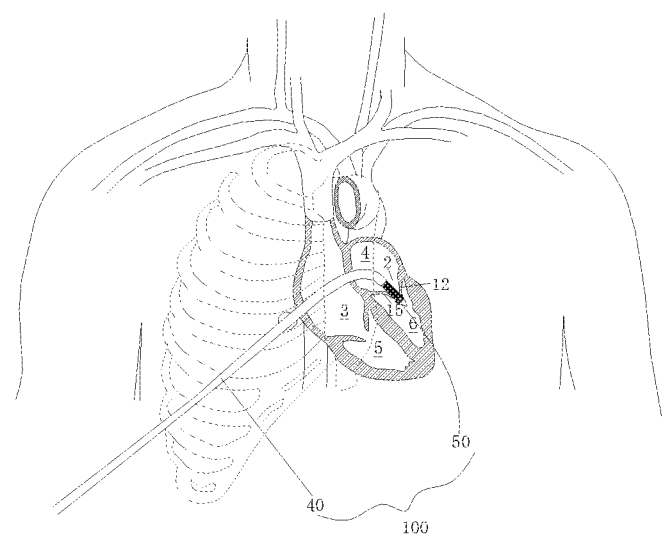
FIG. 2 is a schematic diagram of an interventional medical device replacement system provided by a first embodiment of the present application.

With reference to FIG. 2, an interventional medical device replacement system 100 provided by a first embodiment of the present application includes a delivery device 40, an interventional medical device 50 and a loader (not shown in the figure). The loader is used to load the interventional medical device 50 onto the delivery device 40, and the delivery device 40 is used to deliver the interventional medical device 50 to an implantation position of a heart system to complete implantation of the interventional medical device 50. In this embodiment, the interventional medical device 50 is an artificial mitral valve, and the delivery device 40 implants the interventional medical device 50 into the mitral valve 2 of the heart system.

Delivery Device

Figure 3:
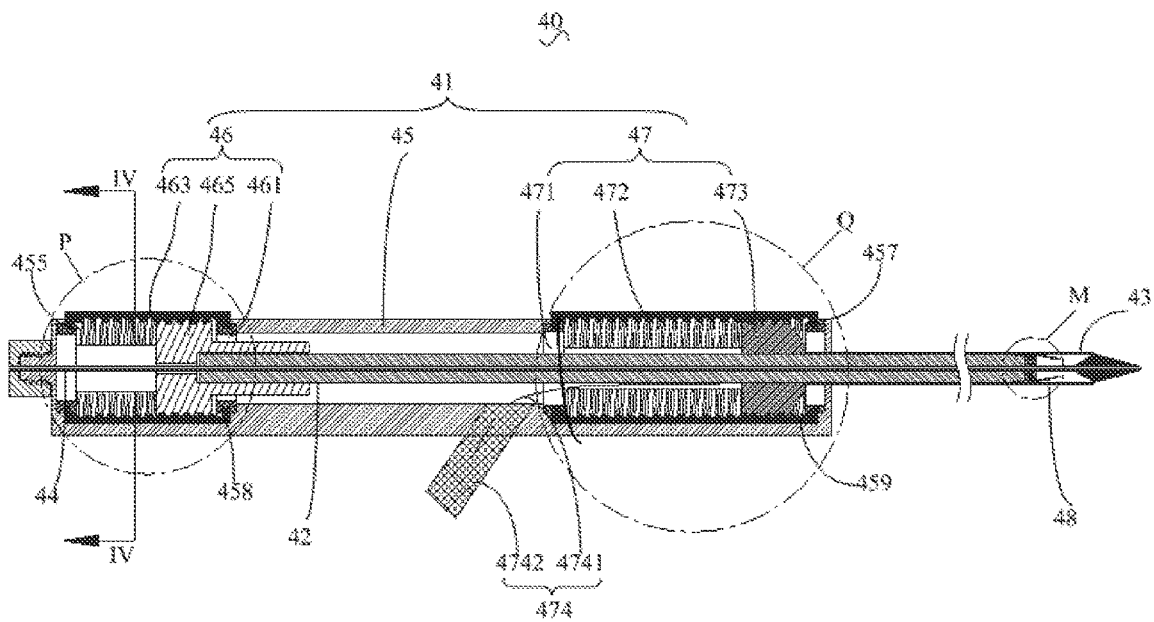
FIG. 3 is a schematic diagram of a delivery device of the interventional medical device replacement system in FIG. 2.

With reference to FIG. 3, the delivery device 40 includes an operating handle 41, a push rod 42, an external sheath 43, an internal sheath core 44 and a device connection assembly 48.

The operating handle 41 includes a handle shell 45, a push rod driving assembly 46 and a sheath driving assembly 47.

Figure 4:
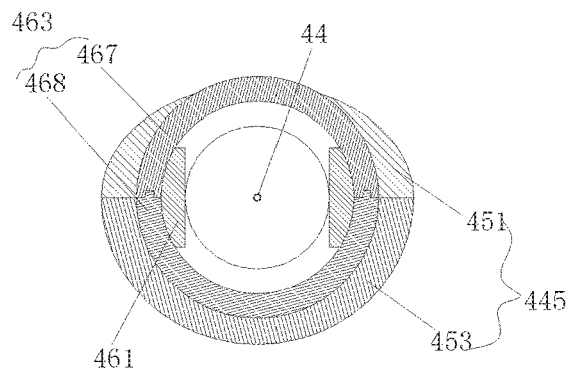
FIG. 4 is a section view of FIG. 3 along the IV-IV line.

With reference to FIG. 4 together with FIG. 3, the handle shell 45 includes an upper shell 451 and a lower shell 453 having the outer diameter different from that of the upper shell 451. After being assembled, the upper shell 451 and the lower shell 453 form an eccentric structure. For example, in this embodiment, the outer diameter of the upper shell 451 is less than that of one, which has the relatively small outer diameter, of the push rod driving assembly 46 and the sheath driving assembly 47; and the outer diameter of the lower shell 453 is greater than that of one, which has the relatively large outer diameter, of the push rod driving assembly 46 and the sheath driving assembly 47. Therefore, the push rod driving assembly 46 and the sheath driving assembly 47 may be partially located inside the shell 45, and also partially located outside the shell 45, and an operator can operate the push rod driving assembly 46 and the sheath driving assembly 47 outside the shell 45 conveniently.

A first containing hole 455 and a second containing hole 457 (as shown in FIG. 3) which are communicated with an inner cavity of the shell 45 are defined in the upper shell 451. The first containing hole 455 is in a T shape on a section including the longitudinal central axial line of the shell 45, and the outer diameter of the end, which is close to the inner cavity of the shell 45, of the first containing hole 455 is greater than that of the end, which is close to the outside of the shell 45, of the first containing hole 455; and the push rod driving assembly 46 is partially contained in the shell 45 and the first containing hole 455, and is partially exposed from the first containing hole 455. The second containing hole 457 is in a T shape on the section including the longitudinal central axial line of the shell 45, and the outer diameter of the end, which is close to the inner cavity of the shell 45, of the second containing hole 457 is greater than that of the end, which is close to the outside of the shell 45, of the second containing hole 457; and the sheath driving assembly 47 is partially contained in the shell 45 and the second containing hole 457, and is partially exposed from the second containing hole 457.

Part of the internal wall of the lower shell 453 is sunken towards its outside to form a first containing slot 458 spatially corresponding to the first containing hole 455 and a second containing slot 459 spatially corresponding to the second containing hole 457. The first containing slot 458 is in a T shape on the section including the longitudinal central axial line of the shell 45, and the outer diameter of a notch of the first containing slot 458 is greater than that of the bottom of the first containing slot 458. The first containing slot 458 is in a T shape on the section including the longitudinal central axial line of the shell 45, and the outer diameter of a notch of the first containing slot 458 is greater than that of the bottom of the first containing slot 458.

Figure 5:
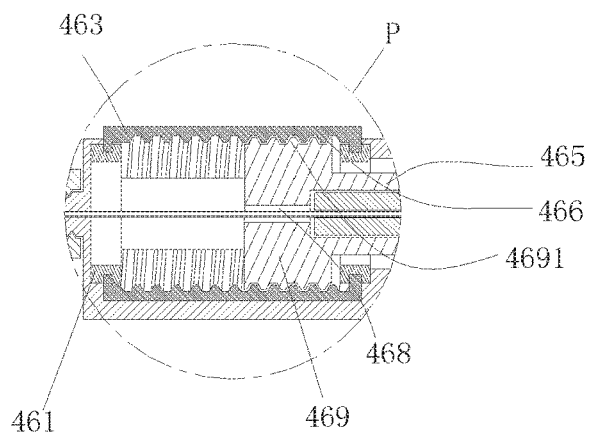
FIG. 5 is an enlarged view of a position P in FIG. 3.
Figure 6:
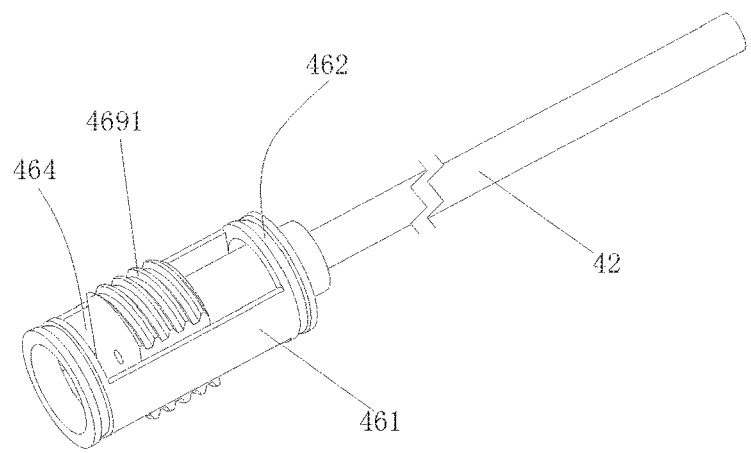
FIG. 6 is a schematic diagram of a local structure of a push rod driving assembly of the delivery device in FIG. 2.

With reference to FIG. 5 and FIG. 6 together, the push rod driving assembly 46 includes a first supporting tube 461, a first rotor 463 surrounding the first supporting tube 461, and a first hollow sliding block 465 which is contained in the first supporting tube 461 and may move along the longitudinal central axis of the first supporting tube 461.

The first supporting tube 461 is contained in a space defined by the first containing hole 455 and the first containing slot 458 in an encircling manner, and is fixed on the internal wall of the shell 45.

First annular slots 462 surrounding the longitudinal central line of the first supporting tube 461 are defined in the side walls of two ends of the first supporting tube 461 along the circumferential direction of the first supporting tube 461.

Two opposite long and narrow box-shaped first guide holes 464 located between the two first annular slots 462 are defined in the side walls of the first supporting tube 461 along the lengthwise direction of the first supporting tube 461.

The first rotor 463 surrounds the first supporting tube 461; one end of the first rotor 463 is movably contained in one first annular slot 462, and the other end of the first rotor 463 is movably contained in the other first annular slot 462. An internal thread 466 is formed on the internal wall of the first rotor 463.

For example, in this embodiment, the inner diameters of the two ends of the first rotor 463 are less than those of other portions of the first rotor 463, so that the ends of the first rotor 463 may be contained in the first annular slots 462, and the middle portion of the first rotor 463 may be separated from the first supporting tube 461; and the first rotor 463 includes two opposite and connected half shells 467 (as shown in FIG. 4).

In a process of assembling the first rotor 463 on the first supporting tube 461, two ends of one half shell 467 may be first arranged in the two first annular slots 462, and then two ends of the other half shell 467 are arranged in the two first annular slots 462, and are connected with the two ends of the half shell 467 in the first annular slots 462 into a whole in a clamping manner.

The first sliding block 465 is contained in the first supporting tube 461, and two opposite sides of the first sliding block 465 protrude from the two first guide holes 464. The first sliding block 465 is in threaded connection with the first rotor 463. The rotation of first rotor 463 drives the first sliding block 465 to move along the axial directions of the first guide holes 464. The distal end of the first sliding block 465 is connected with the push rod 42, so that the axial movement of the first sliding block 465 may drive the push rod 42 to axially move.

In this embodiment, the first sliding block 465 has a T-shaped structure; the outer diameter of the proximal end of the first sliding block 465 is greater than that of the distal end of the first sliding block 465; for the first sliding block 465, its proximal end is contained in the first supporting tube 461, and its distal end protrudes from the first supporting tube 461. The first sliding block 465 has a T-shaped axial through hole 468 penetrating through the end surface of its proximal end and the end surface of its distal end. The outer diameter of the distal end of the axial through hole 468 is greater than that of the proximal end of the axial through hole 468, and the outer diameter of the distal end of the axial through hole 468 is slightly greater than that of the push rod 42, so that the push rod 42 may be contained in the axial through hole 468.

The first sliding block 465 includes a rotor connection portion 469 close to its proximal end. In this embodiment, the rotor connection portion 469 substantially has a cuboid structure, and its opposite parallel side walls are in contact with the opposite internal walls of the first supporting tube 461, respectively; and teeth 4691 used together with the internal thread 466 are arranged on the other pair of parallel side walls of the rotor connection portion 469.

Figure 7:
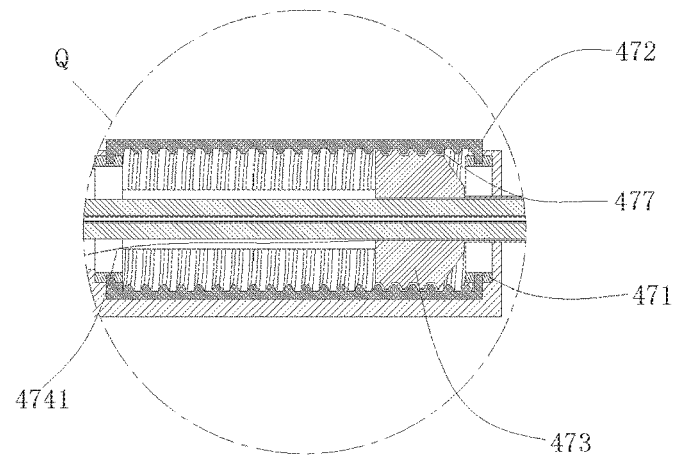
FIG. 7 is an enlarged view of a position Q in FIG. 3.
Figure 8:
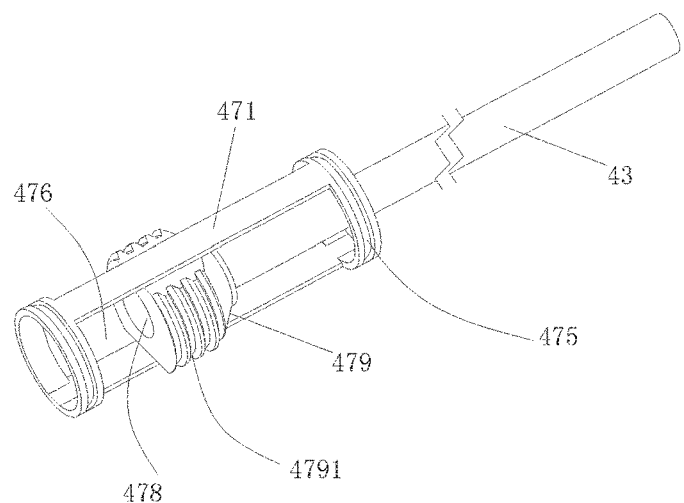
FIG. 8 is a schematic diagram of a local structure of a sheath driving assembly of the delivery device in FIG. 2.

With reference to FIG. 7 and FIG. 8 together, the sheath driving assembly 47 includes a second supporting tube 471, a second rotor 472 surrounding the second supporting tube 471, a second hollow sliding block 473 which is contained in the second supporting tube 471 and may move along the longitudinal central axis of the second supporting tube 471, and a bending unit 474.

The second supporting tube 471 is contained in a space defined by the second containing hole 457 and the second containing slot 459 in an encircling manner, and is fixed on the internal wall of the shell 45. Second annular slots 475 surrounding the longitudinal central line of the second supporting tube 471 are defined in the side walls of two ends of the second supporting tube 471 along the circumferential direction of the second supporting tube 471. Two opposite long and narrow box-shaped second guide holes 476 located between the two second annular slots 475 are defined in the side walls of the second supporting tube 471 along the lengthwise direction of the second supporting tube 471.

The second rotor 472 surrounds the second supporting tube 471; one end of the second rotor 472 is movably contained in one second annular slot 475, and the other end of the second rotor 472 is movably contained in the other second annular slot 475.

In this embodiment, the structure of the second rotor 472 is the same as that of the first rotor 463, and the second rotor 472 also includes an internal thread 477; and the size of the second rotor 472 is also the same as that of the first rotor 463, so that no more detailed description will be given here. It should be understood that in other implementation embodiments, the size of the second rotor 472 may be also different from that of the first rotor 463 and should be set according to an actual requirement.

The second sliding block 473 is contained in the second supporting tube 471, and two opposite sides of the second sliding block 473 protrude from the two second guide holes 476. The second sliding block 473 is in threaded connection with the second rotor 472. The rotation of the second rotor 472 drives the second sliding block 473 to move along the axial directions of the second guide holes 476. The distal end of the second sliding block 473 is connected with the proximal end of the external sheath 43, so that the axial movement of the second sliding block 473 may drive the external sheath 43 to axially move.

The second sliding block 473 also has an axial through hole 478 penetrating through the end surface of its proximal end and the end surface of its distal end. The aperture of the axial through hole 478 is greater than the outer diameter of the push rod 42, so that the proximal end of the push rod 42 may penetrate through the sheath driving assembly 47 to be connected with the first sliding block 465, and the push rod 42 may move relative to the second supporting tube 471 along the axial direction of the second supporting tube 471.

The second sliding block 473 includes a rotor connection portion 479 close to its proximal end. In this embodiment, the rotor connection portion 479 is substantially of a cuboid structure, and its opposite parallel side walls are in contact with the opposite internal walls of the second supporting tube 471 respectively; and teeth 4791 used together with the internal thread 477 are arranged on the other pair of parallel side walls of the rotor connection portion 479.

The bending unit 474 is used to adjust an angle of the distal end of the external sheath 43, and includes a traction wire 4741 connected with the distal end of the external sheath 43, and a driving member 4742 for driving the traction wire 4741 to move. The proximal end of the driving member 4742 is connected with the distal end of the traction wire 4741, and the distal end of the driving member 4742 protrudes from the shell 45, so that the operator can operate the driving member 4742 to drive the traction wire 4741 to move to bend the distal end of the external sheath 43. It should be understood that the structure and the theory of the driving member 4742 may be the same as those of the push rod driving assembly 46, and at the moment, a sliding block of the driving member 4742 is connected with the traction wire 4741; and under the driving of a rotor, the sliding block of the driving member 4742 may drive the traction wire 4741 to move to achieve the aim of the present application, so that no more detailed description will be given here.

The push rod 42 is contained in the external sheath 42, and surrounds the internal sheath core 44. The proximal end of the push rod 42 is connected with the push rod driving assembly 46; the distal end of the push rod 42 penetrates through a shell 411 and extends towards the distal end of the delivery device 40. The rotation of the first rotor 463 may drive the first sliding block 465 to drive the push rod 42 to axially move relative to the shell 411.

The external sheath 43 surrounds the push rod 42, and its proximal end is connected with the sheath driving assembly 47, and its distal end penetrates through the shell 411 and extends towards the distal end of the delivery device 40. The rotation of second rotor 472 may drive the second sliding block 473 to drive the external sheath 43 to axially move relative to the shell 411.

The internal sheath core 44 is contained in the push rod 42, and its proximal end penetrates through the sheath driving assembly 47 and the push rod driving assembly 46 in sequence, and is connected with the shell 411. The distal end of the internal sheath core 44 penetrates through the shell 411, and is farther from the operating handle 41 than the distal end of the push rod 42.

Figure 9:
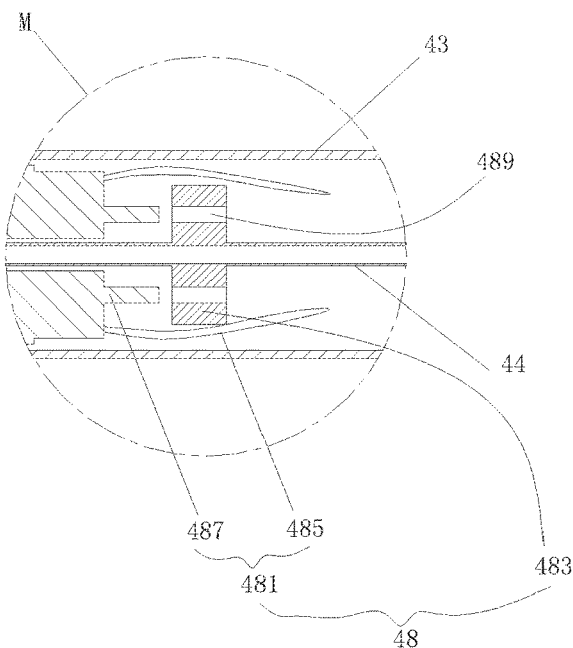
FIG. 9 is an enlarged view of a position M in FIG. 3.
Figure 10:
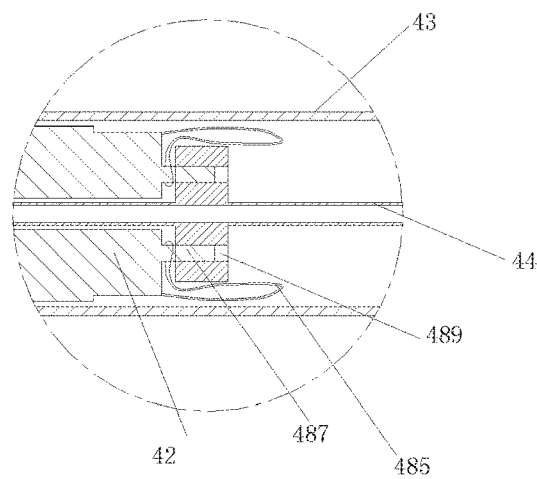
FIG. 10 is a schematic diagram of a state in which a stop member is connected with a connection member in a connection assembly of the delivery device in FIG. 2.

With reference to FIG. 9 and FIG. 10 together, the device connection assembly 48 includes a connection member 481 disposed at the distal end of the push rod 42 and a stop member 483 disposed on the internal sheath core 44. The connection member 481 cooperates with the stop member 483 to control connection and disconnection between the medical device 50 and the delivery device 40.

Figure 11:
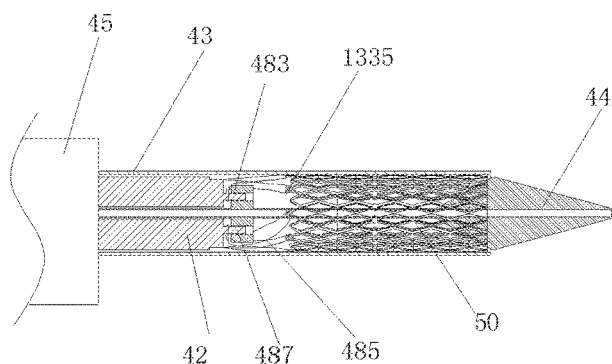
FIG. 11 is a schematic diagram of a connection of the delivery device and the interventional medical device in FIG. 2.

The connection member 481 includes multiple connection rings 485 and multiple connection pillars 487. One end of each connection ring 485 is connected to the push rod 42, and the other end of the connection ring 485 is a free end. One end of each connection pillar 487 is connected to the push rod 42, and the other end of the connection pillar 487 is a free end; and the free end of each connection pillar 487 faces to the stop member 483. In this embodiment, the non-free end of each connection ring 485 and the non-free end of each connection pillar 487 are both connected to the end surface of the distal end of the push rod 42; the number of the connection pillars 487 is equal to that of the connection rings 485, and the multiple connection rings 485 correspond to the multiple connection pillars 487 one by one. Each connection ring 485 is adjacent to each corresponding connection pillar 487. With reference to FIG. 11 together with FIGS. 9 and 10, the stop member 483 is disposed at the distal end of the internal sheath core 44, and is closer to the distal end of the delivery device 40 than the connection member 481. The stop member 483 is equipped with multiple containing bodies 489 to contain the connection pillars 487 sleeved with the connection rings 485. Therefore, after penetrating through the interventional medical device 50, the free ends of the connection rings 485 sleeve the connection pillars 487; after the connection pillars 487 sleeved with the connection rings 485 are contained in the containing bodies 489, the connection rings 485 can not be separated from the connection pillars 487 in the absence of the action of an external force, so that the interventional medical device 50 is connected with the delivery device 40; after the connection pillars 487 sleeved with the connection rings 485 are separated from the containing bodies 489 under the action of an external force, the interventional medical device 50 is separated from the delivery device 40, thus completing releasing of the interventional medical device 50.

In this embodiment, the stop member 483 surrounds the internal sheath core 44, and is fixedly disposed on the external wall of the internal sheath core 44; the containing bodies 489 are through holes penetrating through the proximal end and the distal end of the stop member 483; the number of the containing bodies 489 is equal to that of the connection pillars 487, and the multiple containing bodies 489 correspond to the multiple connection pillars 487 one by one; and the aperture of each containing body 489 is greater than or equal to the outer diameter of each corresponding connection pillar 487, so that one connection pillar 487 may be contained in one corresponding containing body 489.

In the present application, as the connection rings 485 used to connect the interventional medical device 50 with the delivery device are soft structures, they do not typically cause damage to human tissues, and are simple in structure and easy to manufacture.

Interventional Medical Device

Figure 12:
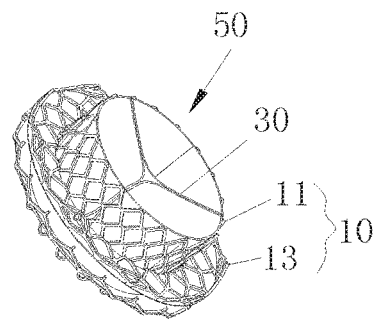
Figure 13:
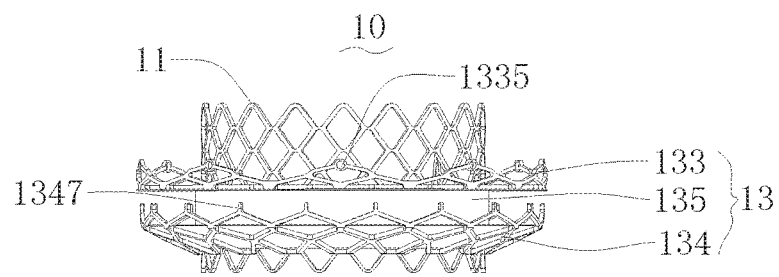

With reference to FIG. 12 and FIG. 13, the interventional medical device 50 provided by the first embodiment of the present application is used to replace a diseased mitral valve, and includes an artificial heart valve stent 10 and an artificial valve leaflet 30 arranged in the artificial heart valve stent 10.

The artificial heart valve stent 10 includes a tubular stent body 11 and a valve annulus sealing member 13 surrounding the external wall of the stent body. In this embodiment, the stent body 11 and the valve annulus sealing member 13 are independently formed, and then are fixedly connected into a whole body, thus improving the overall intensity of the artificial heart valve stent 10 and prolonging the lifetime of the interventional medical device 50.

The tubular stent body 11 is of a meshed structure formed by weaving a wire or cutting a tube and then shaping the woven wire or the cut tube, and is used to carry the artificial valve leaflet 30. Preferably, in this embodiment, the tubular stent body 11 is of a meshed structure formed by cutting a nickel-titanium metal tube and shaping the cut tube. It should be understood that in other embodiments, the stent body may be also formed by weaving a nickel-titanium wire and shaping the woven wire, or the stent body may be also formed by weaving a macromolecular wire (such as a polycarbonate wire, a polypropylene wire and a polyamide wire) made of a macromolecular material or cutting a macromolecular tube made of the macromolecular material and shaping the woven wire or the cut tube.

Figure 14:
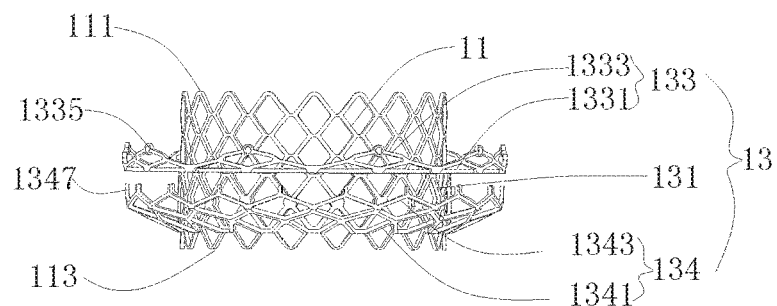
FIG. 14 is a schematic diagram of a flow resisting film-removed stent of the interventional medical device in FIG. 12.
Figure 15:
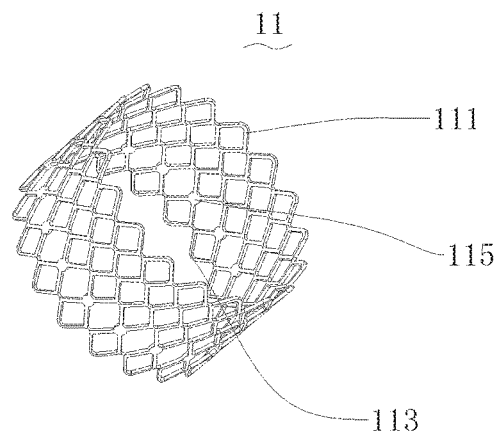
FIG. 15 is a schematic diagram of a structure of a stent body of the stent in FIG. 14.

With reference to FIG. 14 and FIG. 15 together, the stent body 11 includes an inflow side end 111 and an outflow side end 113 opposite to the inflow side end. Multiple welding spots 115 are arranged on patterns of the stent body 11. The multiple welding spots 115 are uniformly distributed along the same circumferential direction of the stent body 11 in a spacing manner; a connection line of the multiple welding spots 115 is coaxial with the middle axial line of the stent body 11, and the welding spots 115 are configured for welding the valve annulus sealing member 13. In this embodiment, the contour lines of the welding spots 115 are polygonal, and the diameter of a polygonal incircle is in a range from 0.5 mm to 2 mm, and is at least greater than the diameter of a welding pool. In this embodiment, the distance between the centers of the welding spots 115 and the inflow side end 111 is greater than that between the centers of the welding spots 115 and the outflow side end 113.

With reference to FIG. 13 and FIG. 14 again, the valve annulus sealing member 13 includes a hollow tubular connection stent 131 connected with the stent body 11, an inflow side skirt 133 which is connected with one end of the tubular connection stent 131 and extends outwards, an outflow side skirt 134 which is connected with the other end of the tubular connection stent 131 and extends outwards, and flow resisting cloth 135, wherein the connection stent 131 is of a meshed structure formed by weaving a wire or cutting a tube and shaping the woven wire or the cut tube. For example, in this embodiment, the connection stent 131 is of a meshed structure formed by cutting a nickel-titanium metal tube and shaping the cut tube; and the inflow side skirt 133, the outflow side skirt 134 and the tubular connection stent 131 are integrally formed. It should be understood that in other embodiments, the connection stent may be also formed by weaving a nickel-titanium wire and shaping the woven wire, and the connection stent may be also formed by weaving a macromolecular wire (such as a polycarbonate wire, a polypropylene wire and a polyamide wire) made of a macromolecular material or cutting a macromolecular tube made of the macromolecular material and shaping the woven wire or the cut tube. The free ends of both the inflow side skirt 133 and the outflow side skirt 134 extend towards the inflow side end 111. The inflow side skirt 133 is used for cooperating with the outflow side skirt 134 to clamp artificial heart valve tissues. The distance between the end, which is connected with the stent body 11, of the inflow side skirt 133 and the end, which is connected with the stent body 11, of the outflow side skirt 134 ranges from 2 mm to 6 mm. The flow resisting cloth 135 is disposed on at least one of the inflow side skirt 133 and the outflow side skirt 134, and is used to prevent blood from flowing back at the valve annulus sealing member 13 so as to prevent perivalvular leakage. In this embodiment, the artificial heart valve tissues clamped by cooperation of the inflow side skirt 133 and the outflow side skirt 134 include a mitral annulus 8, a valve leaflet 15 and a valve leaflet 12; the flow resisting cloth 135 is disposed on the surface, which faces to the outflow side end 113, of the inflow side skirt 133, the external wall, which is located between the inflow side skirt 133 and the outflow side skirt 134, of the connection stent 131, and the surface, which faces to the inflow side end 111, of the outflow side skirt 134. In some other embodiments, the flow resisting cloth 135 may be only disposed on the inflow side skirt 133 or the outflow side skirt 134.

Figure 16:
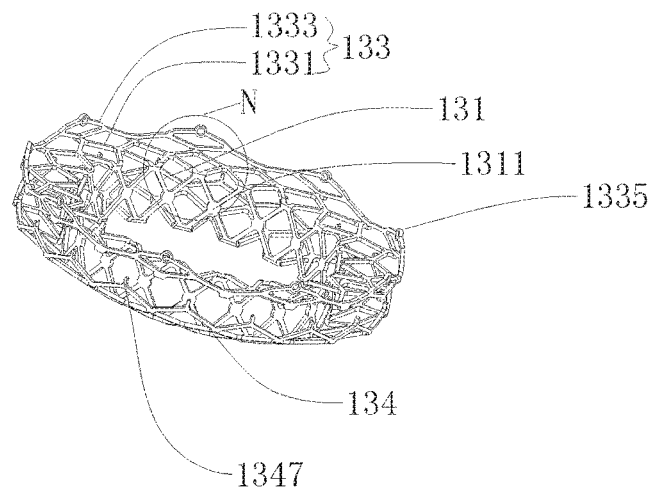
FIG. 16 is a schematic diagram of a flow resisting film-removed valve annulus sealing member in FIG. 14.

With further reference to FIG. 16, the connection stent 131 has multiple welding spots 1311. The welding spots 1311 are used together with the welding spots 115 on the stent body 11 for welding; the shapes and the sizes of the welding spots 1311 are respectively the same as the shapes and the sizes of the welding spots 115; and the welding may be laser electric welding or electric resistance welding.

Figure 17:
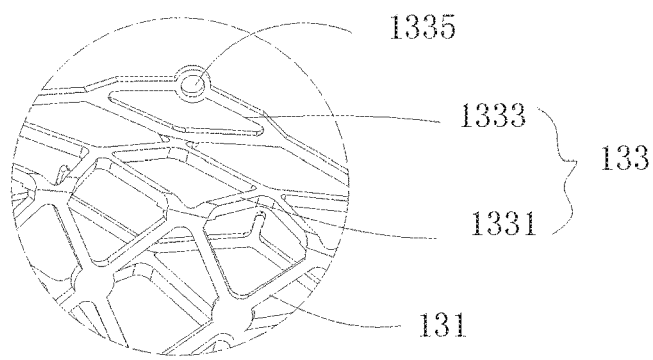
FIG. 17 is an enlarged view of a position N in FIG. 16.
Figure 18:
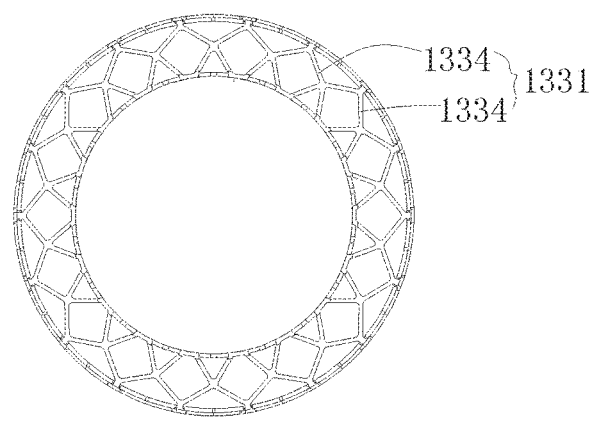
FIG. 18 is a top view seen from the side of an outflow side skirt in FIG. 16.

With reference to FIG. 17 and FIG. 18 together, the inflow side skirt 133 surrounds the tubular connection stent 131, and includes an inflow side clamping portion 1331 which is connected with the connection stent 131 and surrounds the connection stent 131, and an inflow side upwarping portion 1333 which is connected with the inflow side clamping portion 1331 and surrounds the inflow side clamping portion 1331. The inflow side clamping portion 1331 is located between the inflow side upwarping portion 1333 and the connection stent 131. In this embodiment, when the valve annulus sealing member 13 is connected to the stent body 11, a projection of the end, which is connected with the tubular stent body 11, of the inflow side skirt 133 on a section parallel to the longitudinal central axial line of the tubular stent body 11 is separated from a projection of the inflow side end 111 on the section parallel to the longitudinal central axial line of the tubular stent body 11, that is, the inflow side skirt 133 is connected to any other actually required portions on the stent body 11 other than the inflow side end 111. It should be understood that the inflow side skirt 133 also may be connected to the inflow side end 111 of the stent body 11.

The inflow side clamping portion 1331 is connected between the connection stent 131 and the inflow side upwarping portion 1333, and is formed by extending outwards from the external wall of the connection stent 131. In this embodiment, in a spread state, the inflow side clamping portion 1331 is substantially parallel to a section perpendicular to the longitudinal central axis of the connection stent 131; the inflow side clamping portion 1331 includes multiple rhombic grids 1334. The centers of the multiple rhombic grids 1334 are connected to form an annular structure surrounding the connection stent 131.

The inflow side upwarping portion 1333 is formed by extending from the outer edge of the inflow side clamping portion 1331 to a direction getting close to the inflow side end 111. The end, which is far away from the inflow side clamping portion 1331, of the inflow side upwarping portion 1333 is the free end of the inflow side skirt 133, and in the spread state, an included angle is formed between the inflow side upwarping portion 1333 and the inflow side clamping portion 1331. Therefore, the inflow side skirt 133 is placed on the mitral annulus 6 after the interventional medical device is implanted so as to prevent the edge of the inflow side skirt 133 from cutting the left atrium. In this embodiment, in the spread state, the included angle between the inflow side upwarping portion 1333 and the inflow side clamping portion 1331 is 90 degrees. It should be understood that in the spread state, the included angle between the inflow side upwarping portion 1333 and the inflow side clamping portion 1331 also may be a set degree as required, such as 30 degrees, 60 degrees or 120 degrees, not limited to 90 degrees in this embodiment.

Multiple connection elements 1335 for connecting a delivery system (not shown in the figure) are further arranged at the edge, which extends towards the inflow side end 111, of the inflow side upwarping portion 1333. In an exemplary embodiment, an inflow side waveform structure surrounding the connection stent 131 is formed at the edge of the free end of the inflow side upwarping portion 1333; the connection elements 1335 are connection holes, and are located at wave peaks of the inflow side waveform structure. It should be understood that the connection elements 1335 may be also connection hooks.

It should be understood that multiple inflow side anchoring members with free ends facing to the left ventricle (namely the outflow side end 113) are also arranged on the inflow side skirt 133. It should be further understood that the inflow side anchoring members also may be disposed on the inflow side upwarping portion 1333, and their disposal positions may be set according to an actual requirement.

With reference to FIG. 13, FIG. 14 and FIG. 16 again, the outflow side skirt 134 surrounds the tubular connection stent 131, and includes an outflow side clamping portion 1341 which is connected with the connection stent 131 and surrounds the connection stent 131, and an outflow side upwarping portion 1343 which is connected with the outflow side clamping portion 1341 and surrounds the outflow side clamping portion 1341. The outflow side clamping portion 1341 is located between the outflow side upwarping portion 1343 and the connection stent 131.

In this embodiment, a projection of the end, which is connected with the stent body 11, of the outflow side skirt 134 on a section parallel to the longitudinal central axial line of the stent body 11 is separated from a projection of the outflow side end 113 on the section parallel to the longitudinal central axial line of the stent body 11; and the distance between the end, which is connected with the stent body 11, of the outflow side skirt 134 and the outflow side end 113 is less than the distance between the end, which is connected with the stent body 11, of the inflow side skirt 133 and the inflow side end 111 so as to reduce the risk of outflow tract obstruction.

It should be understood that the outflow side skirt 134 also may be connected to the outflow side end 113 of the stent body 11. It should be further understood that the distance between the end, which is connected with the stent body 11, of the outflow side skirt 134 and the outflow side end 113 also may be equal to the distance between the end, which is connected with the stent body 11, of the inflow side skirt 133 and the inflow side end 111.

The outflow side clamping portion 1341 is connected between the connection stent 131 and the outflow side upwarping portion 1343, and is formed by extending outwards from the external wall of the connection stent 131. The distance between the end, which is connected with the connection stent 131, of the outflow side clamping portion 1341 and the end, which is connected with the connection stent 131, of the inflow side clamping portion 1331 ranges from 2 to 6 mm.

In this embodiment, in the spread state, an acute angle is formed between the outflow side clamping portion 1341 and the longitudinal central axis of the connection stent 131; the distance between the end, which is connected with the connection stent 131, of the outflow side clamping portion 1341 and the end, which is connected with the connection stent 131, of the inflow side clamping portion 1331 is 6 mm; and the distance between the outflow side clamping portion 1341 and the inflow side clamping portion 1331 along the longitudinal central axial line of the connection stent 131 is gradually reduced outwards from the connection stent 131.

The outflow side upwarping portion 1343 is formed by extending from the outer edge of the outflow side clamping portion 1341 to a direction getting close to the inflow side end 111. The end, which is distant from the outflow side clamping portion 1341, of the outflow side upwarping portion 1343 is the free end of the inflow side skirt 133. In this embodiment, the outflow side upwarping portion 1343 is of an outflow side waveform structure surrounding the stent body 11, and in the spread state, the outflow side upwarping portion 1343 is parallel to the longitudinal central axis of the connection stent 131.

Multiple outflow side anchoring members 1347 are also arranged on the outflow side skirt 134, and the free ends of the outflow side anchoring members 1347 face to the left ventricle (namely the outflow side end 113). The anchoring members 1347 are used to fix the artificial heart valve 100 on the mitral annulus 8 when the artificial heart valve 100 is spread. In this embodiment, the outflow side anchoring members 1347 are arranged on wave peaks of the outflow side waveform structure of the outflow upwarping portion 1343. It should be understood that the outflow side anchoring members 1347 also may be disposed on the outflow side clamping portion 1341, and their disposal positions may be set according to an actual requirement.

Compared with the prior art, the artificial heart valve in the embodiment of the present application has the following obvious advantages:

(1) the inflow side skirt and the outflow side skirt of the artificial heart valve stent cooperate with each other to clamp the artificial heart valve tissues, so that the artificial heart valve stent may be steadily arranged on the artificial heart valve tissues, prolong the lifetime of the artificial heart valve having the artificial heart valve stent and reduce the risk of another valve replacement for a patient;

(2) the stent body and the connection stent of the artificial heart valve stent are independently formed, and then are fixedly connected into a whole body, so that in a manufacturing process of the skirts of the connection stent, the structural integrity and the mechanical property of the stent body may not be reduced, and in a use process, under the action of buffering of the connection portions of the connection stent, a force applied by the artificial heart valve tissues to the skirts of the connection stent is difficultly all transmitted to the stent body, so that it is hard to change the shape and the size of the stent body and affect the hydromechanical performance of the valve leaflets;

(3) the connection holes are defined in the skirts on the atrial side of the artificial heart valve stent, so that releasing and recycling of the artificial heart valve are facilitated;

(4) the artificial heart valve stent is equipped with the anchoring members, so that the stability of the artificial heart valve having the artificial heart valve stent is improved after the artificial heart valve is implanted;

(5) the artificial heart valve stent is equipped with the flow resisting cloth, so that occurrence of the perivalvular leakage after the artificial heart valve is implanted may be effectively prevented.

It should be noted that as the interventional medical device 50 should be stored in an anti-calcification solution, the delivery device 40 and the interventional medical device 50 should be packaged separately. Before the surgery, the interventional medical device 50 is loaded into the delivery device 40. The method for loading the interventional medical device 50 into the delivery device 40 includes the following steps: first, putting the free ends of the connection rings 485 into the connection elements 1335 of the interventional medical device 50 in a penetrating manner, and sleeving the connection pillars 487 with the connection rings 485; then driving the push rod 42 to drive the connection pillars 487 to move towards the stop member 483 until the connection pillars 487 are contained in the containing bodies 489 of the stop member 483; and slowly and completely loading the interventional medical device 50 into the distal end of the external sheath 43.

Surgical Method

A detailed description will follow regarding a method for replacing a pathologically changed mitral valve by adopting the delivery device 40 and the interventional medical device 50.

Figure 19:
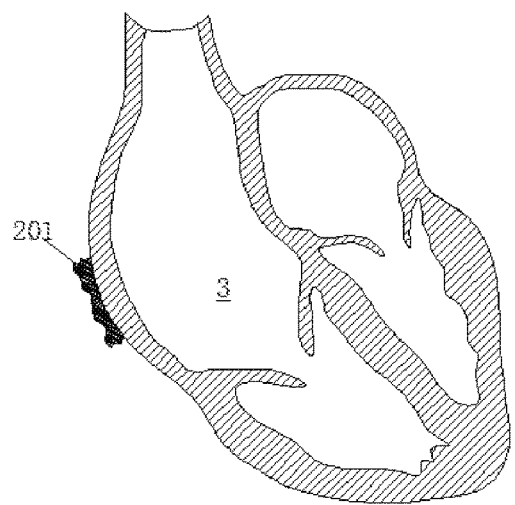
FIG. 19 is a schematic diagram of the right atrial appendage equipped with a pocket.

A first implantation method is carried out under the assistance of a thoracoscope, including:

With reference to FIG. 19, step I, a suturing a mattress type pocket 201 at the right atrial appendage, includes: first, after a patient lies down about 30 degrees on the left, forming a small incision which is about 3 cm beside the fourth intercostal sternum of the right thorax, specifically, incising the skin, subcutaneous tissues and muscular layer fascia in sequence, and performing blunt dissection on the muscular layer until the pleural cavity; second, exposing the pericardium; then incising the pericardium and suspending the pericardium to expose the right atrium; and suturing the mattress type pocket 201 at the right atrial appendage. In other embodiments, according to an individual difference and an actual requirement of a patient, the patient can lie down a certain angle ranging from about 30 degrees to 45 degrees. It should be understood that in other embodiments, according to the individual difference and the actual requirement of the patient, another mattress type pocket also may be sutured on the anterolateral wall of the right atrium to facilitate entry of a puncture needle into the left atrium 4 in the subsequent step. It should be understood that in other embodiments, according to the individual difference and the actual requirement of the patient, in order to facilitate the surgical operation, two or more small incisions other than the incision required by the thoracoscope also may be formed in the right thorax, not limited to one small incision other than the incision utilized by the thoracoscope in this embodiment.

Figure 20:
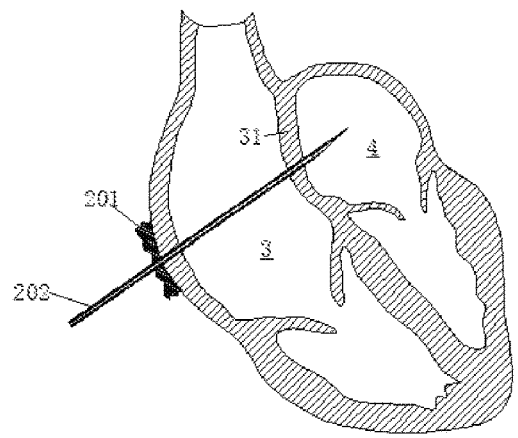
FIG. 20 is a schematic diagram of the left atrium after a puncture needle enters the left atrium via the pocket in FIG. 19.

With reference to FIG. 20 together, step II, delivering the tip of the puncture needle 202 into the left atrium 4, specifically, enabling the needle tip of the puncture needle 202 to puncture into the right atrium 3 from the middle portion of the mattress type pocket 201 and then puncture into the left atrium 4 through the atrial septum 31. It should be understood that in other embodiments, according to the individual difference and the actual requirement of the patient, the needle tip of the puncture needle 202 also may puncture into the left atrium 4 through the fossa ovalis 301.

Figure 21:
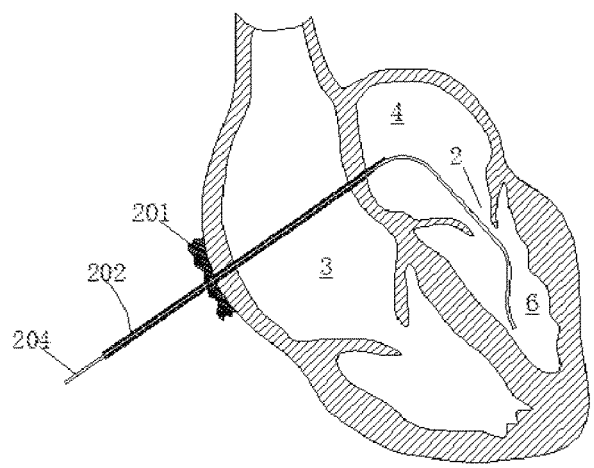
FIG. 21 is a schematic diagram of the left ventricle after a guide wire reaches the left ventricle via the inner cavity of the puncture needle in FIG. 20.

With reference to FIG. 21 together, step III, delivering the distal end of a guide wire 204 into the left atrium 4 along an inner cavity of the puncture needle 202, and into the left ventricle 6 through the mitral valve 2.

Step IV, removing the puncture needle 202 from the heart system.

Figure 22:
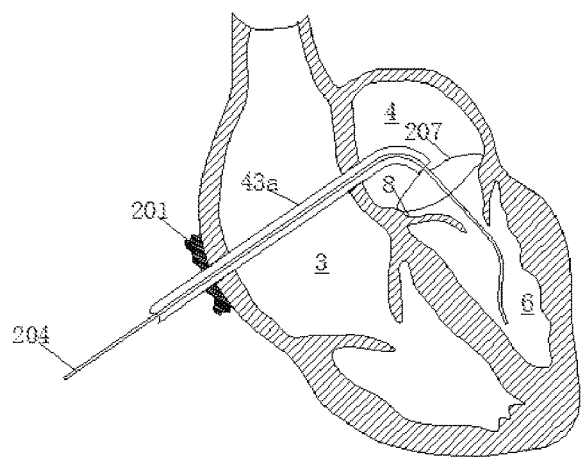
FIG. 22 is a schematic diagram of a measurement of the size of a valve annulus.

Step V, with reference to FIG. 22 together, measuring the size of the mitral annulus 8. Specifically, first, delivering the distal end of a delivery system 43a with a valve measurer 207 to the left atrium 4 along the guide wire 204; second, releasing the valve measurer 207 from the delivery system 43a, and measuring the size of the mitral annulus 8; and finally, recycling the valve measurer 207 into the delivery system 43a.

Step VI, removing the delivery system 43a with the valve measurer 207 from the heart system, and selecting an interventional medical device 50 of a proper specification according to the measured size of the mitral annulus 8. It should be understood that in other embodiments, if the size of the mitral annulus 8 is measured through ultrasonic and/or computerized tomography before the surgery, steps V and VI may be omitted.

Figure 23:
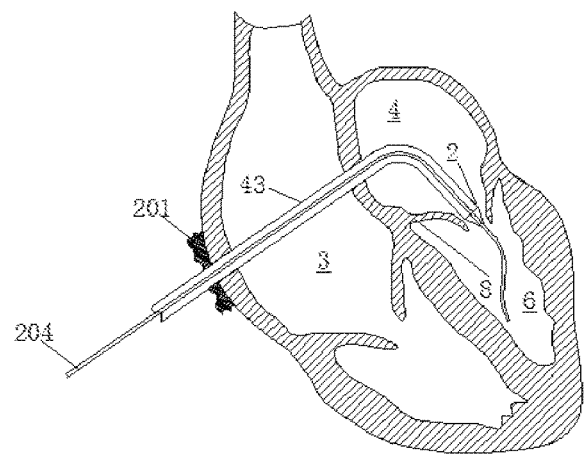
FIG. 23 is a schematic diagram of the mitral valve after an interventional medical device-loaded delivery device reaches the mitral valve along a guide wire.

With reference to FIG. 23 together, step VII, delivering the distal end of a delivery device 40 with the interventional medical device 50 of the proper specification to the left ventricle 6 along the guide wire 204, tightening the mattress type pocket 201, and adjusting the angle of the distal end of the external sheath 43 through the bending unit 474 to enable the distal end of the external sheath 43 to be perpendicular to a plane where the mitral annulus 8 is placed.

Step VIII, removing the guide wire 204 from the heart system.

Step IX, completely exposing the interventional medical device 50 from the delivery device 40, and fixing it on the mitral tissue.

Figure 24:
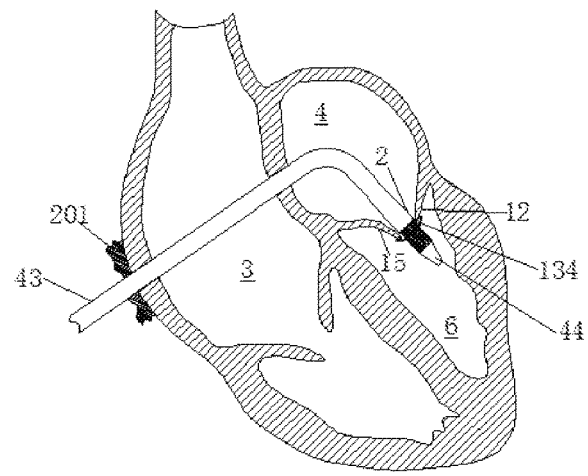
FIG. 24 is a schematic diagram of partial exposure of the interventional medical device in the heart system from the delivery device.
Figure 25:
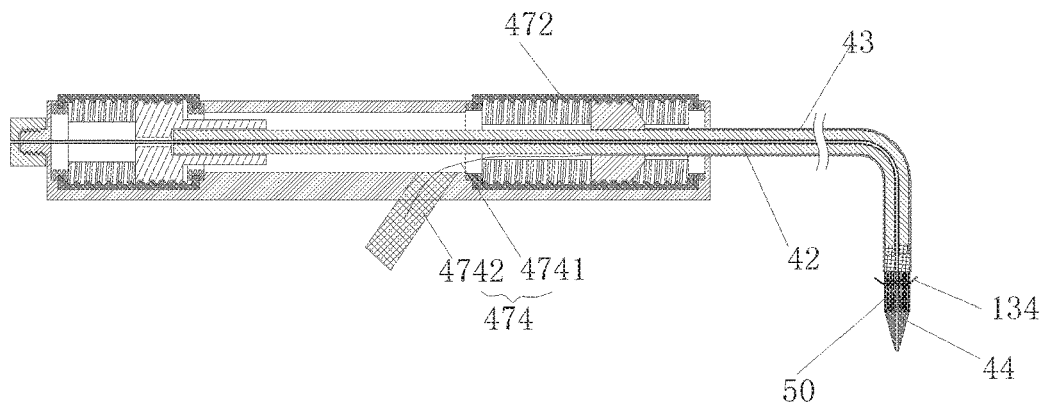
FIG. 25 is a schematic diagram of a positional relation between the partially exposed interventional medical device and the delivery device.
Figure 26:
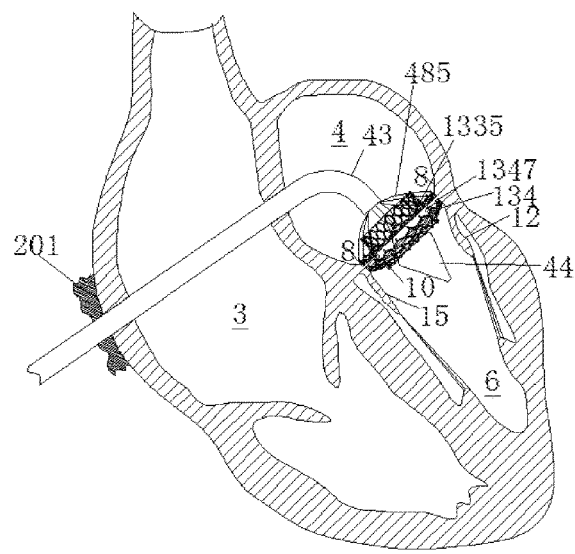
FIG. 26 is a schematic diagram of a full exposure of the interventional medical device in the heart system from the delivery device.
Figure 27:
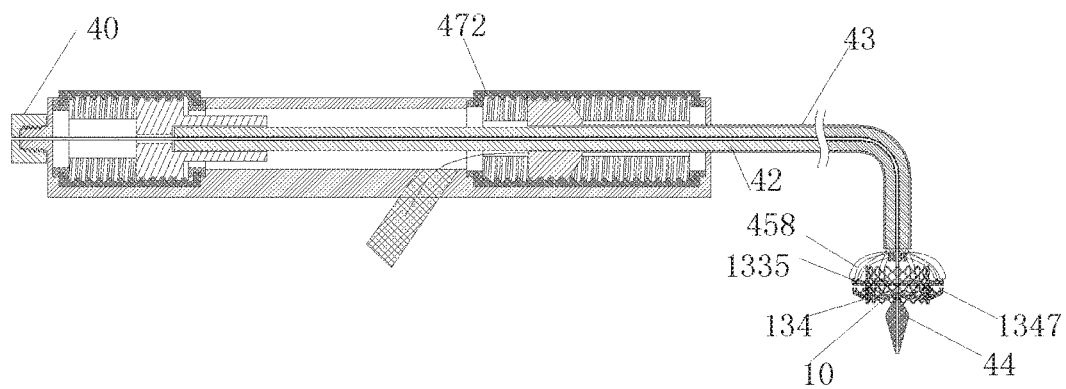
FIG. 27 is a schematic diagram of a positional relation between the fully exposed interventional medical device and the delivery device.

Specifically, first, rotating a second rotor 472 to drive the external sheath 43 to slowly move towards the proximal end of the delivery device 40 relative to a push rod 42 to gradually expose the interventional medical device 50 until an outflow side skirt 134 of the interventional medical device is exposed from the external sheath 43; second, adjusting a driving member 4742 of the bending unit 474 to drive a traction wire 4741 of the bending unit 474 to adjust the angle of the distal end of the external sheath 43 so as to enable mitral valve leaflets 15 and 12 to be placed in an included angle between the outflow side skirt 134 and a stent body 10 (as shown in FIG. 24 and FIG. 25); then continuously rotating the second rotor 472 to drive the external sheath 43 to slowly move towards the proximal end of the delivery device 40 relative to the push rod 42 to gradually completely push the interventional medical device 50 out of the external sheath 43 and enable outflow side anchoring members 1347 on the outflow side skirt 134 to be inserted into the mitral annulus 8 so as to improve the stability of the interventional medical device 50 in the body (as shown in FIG. 26 and FIG. 27). At the moment, connection elements 1335 on the interventional medical device 50 are connected with the distal end of the push rod 42 through connection rings 458. If the position of the interventional medical device 50 is not as desired, the second rotor 472 may be rotated to drive the external sheath 43 to move forwards until the interventional medical device 50 is completely contained in the sheath 43; after the position is adjusted, the interventional medical device 50 is completely re-exposed from the delivery device 40, and is fixed on the mitral tissue.

Figure 28:
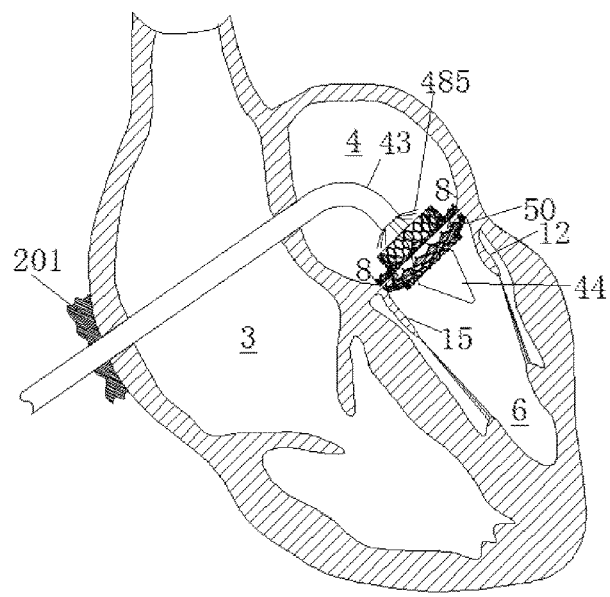
FIG. 28 is a schematic diagram of the released interventional medical device in the heart system.
Figure 29:
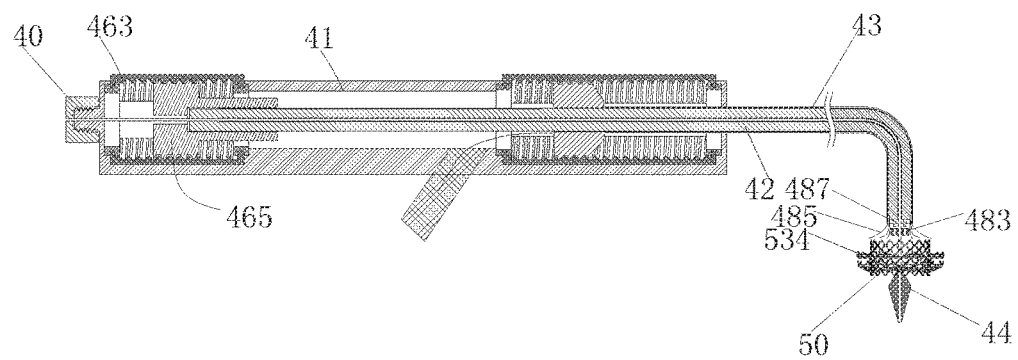
FIG. 29 is a schematic diagram of complete separation of the interventional medical device from the delivery device.

Step X, releasing the interventional medical device 50 from the delivery device 40. Specifically, first, under the condition of keeping the external sheath 43 static relative to the shell 411, rotating a first rotor 463 to drive a first sliding block 465 and the push rod 42 connected with the first sliding block 465 to slowly move towards the proximal end relative to the shell 411, and enabling the push rod 42 moving towards the proximal end to drive a connection member 481 to get away from a stop member 483 to relieve restriction of connection pillars 487 to the connection rings 485, thus releasing the interventional medical device 50 from the delivery device 40 (as shown in FIG. 28 and FIG. 29).

Figure 30:
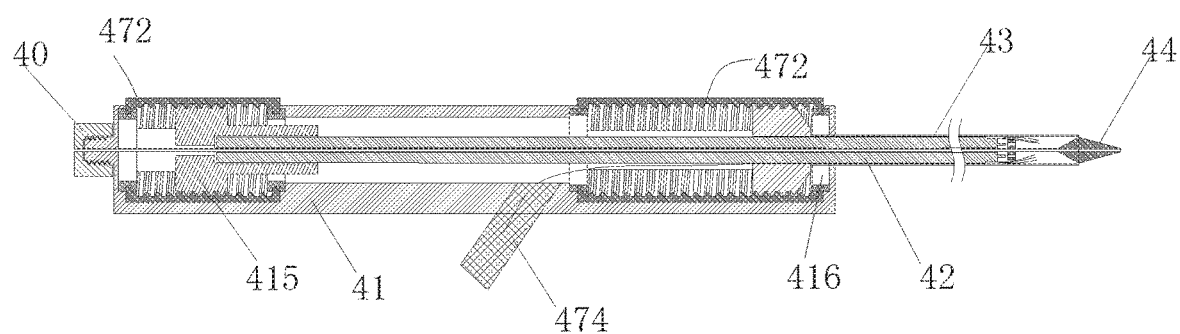
FIG. 30 is a schematic diagram of closure of an internal sheath core and an external sheath of the delivery device.
Figure 31:
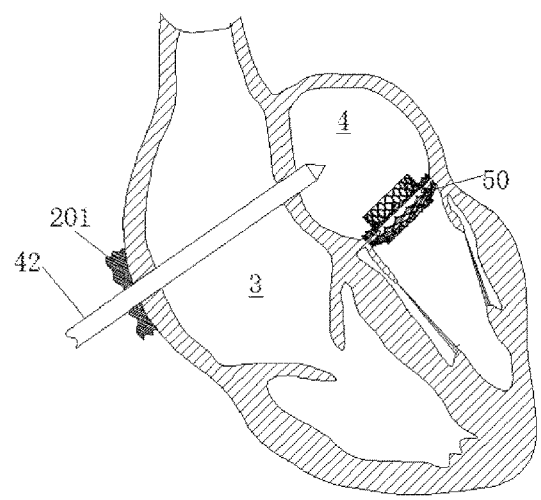
FIG. 31 is a schematic diagram of closure of an internal sheath core and an external sheath in the heart system.

Step XI, recycling an internal sheath core 44 into the external sheath 43, and adjusting the distal end and the proximal end of the external sheath 43 to be on the same straight line. Specifically, first, under the condition that the push rod 42 is static relative to the shell 41, rotating the second rotor 472 to drive the distal end of the external sheath 43 to slowly move towards the distal end of the internal sheath core 44 until the distal end of the internal sheath core 44 is recycled into the external sheath 43; second, adjusting the distal end and the proximal end of the external sheath 43 by the bending unit 471 to be on the same straight line (as shown in FIG. 30 and FIG. 31).

Figure 32:
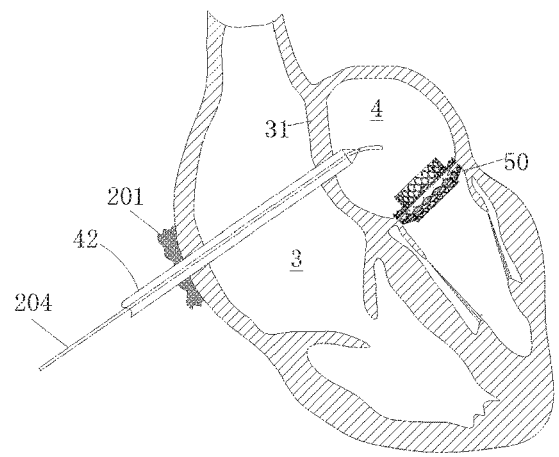
FIG. 32 is a schematic diagram of the left atrium after a guide wire enters the left atrium via the delivery device.

With reference to FIG. 32, step XII, putting the distal end of the guide wire 204 into the left atrium 4 again along an inner cavity of the internal sheath core 44 in the delivery device 40, then removing the delivery device 40, and remaining the guide wire 204 in the left atrium 4.

Figure 33:
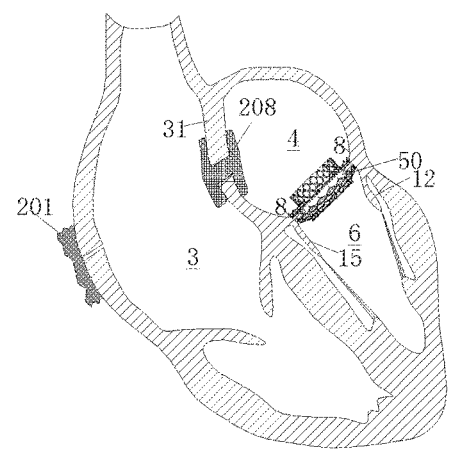
FIG. 33 is a schematic diagram of disposal of an occluder for occluding a puncture hole of the atrial septum and ligation of a pocket.

Step XIII, checking whether there is residual shunt at the punctured portion of the atrial septum 31 through ultrasonic imaging. If the residual shunt is obvious, carrying out atrial septum occlusion, that is, implanting an occluder 208 under the guide of the guide wire 204 to occlude the punctured portion of the atrial septum 31 (as shown in FIG. 33); and if there is no residual shunt, removing the guide wire 204 from the heart system, ligating the pocket 201, and suturing the small incision in the right thorax, thus completing the whole surgical procedure.

Compared with the prior art, the implantation method of the present application has the following advantages:

(1) in the surgical procedure of the present application, no extracorporeal circulation is needed, so that the harm of a large surgical trauma is avoided;

(2) in the surgical procedure of the present application, puncturing is implemented via the small incision in the right thorax instead of a vascular path, so that the size of a blood vessel may not limit the size of the interventional medical device, and the structural design of the interventional medical device is flexible;

(3) in the surgical procedure of the present application, the puncturing is carried out via the right atrium which has the blood pressure less than that of the left ventricle and has a thinner muscular layer, so that no bleeding or a small bleeding amount is caused at a puncture point, and the puncturing is easy to carry out;

(4) an interventional medical device recycling device of the present application is arranged in the left atrium to avoid incidence of left ventricular outflow tract obstruction and improve the surgical safety;

(5) in the surgical procedure of the present application, the delivery device for carrying the interventional medical device is relatively far from the chordae tendineae to prevent the delivery device or the interventional medical device from touching the chordae tendineae, thus reducing the incidence of a phenomenon that the chordae tendineae twines around the delivery device or the interventional medical device, and making the surgery safer.

A second method for implanting an interventional medical device includes: I, which is the same as that in the first implantation method, no more detailed description will be given here.

Figure 34:
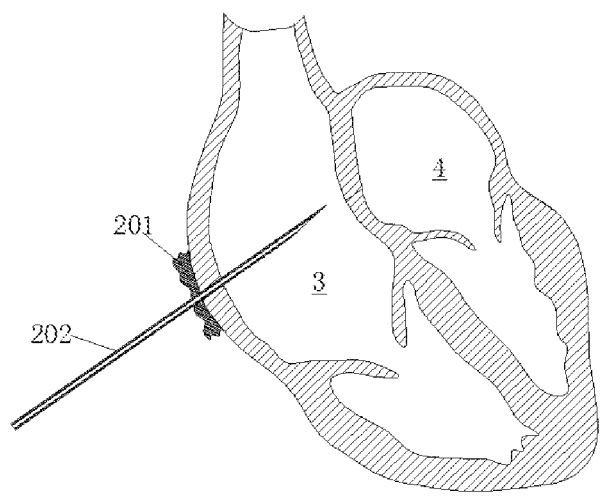
FIG. 34 is a schematic diagram of the right atrium after a puncture needle enters the right atrium via a pocket in a second implantation method.

Step II, with reference to FIG. 34, enabling the needle tip of the puncture needle 202 to puncture into the right atrium 3 from the middle portion of the mattress type pocket 201.

Figure 35:
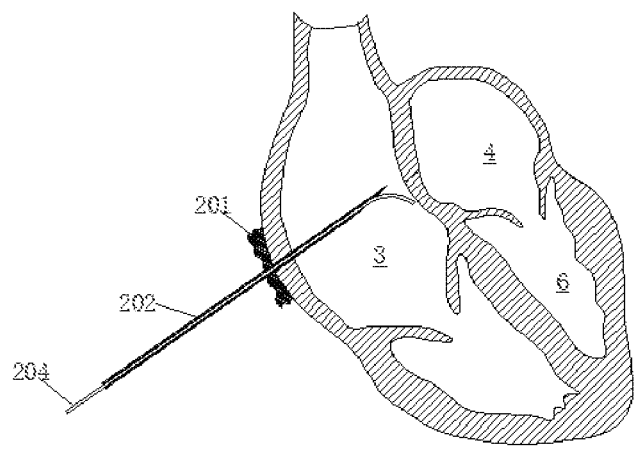
FIG. 35 is a schematic diagram of the right atrium after the distal end of a guide wire is delivered into the right atrium along an inner cavity of the puncture needle in FIG. 34.
Figure 36:
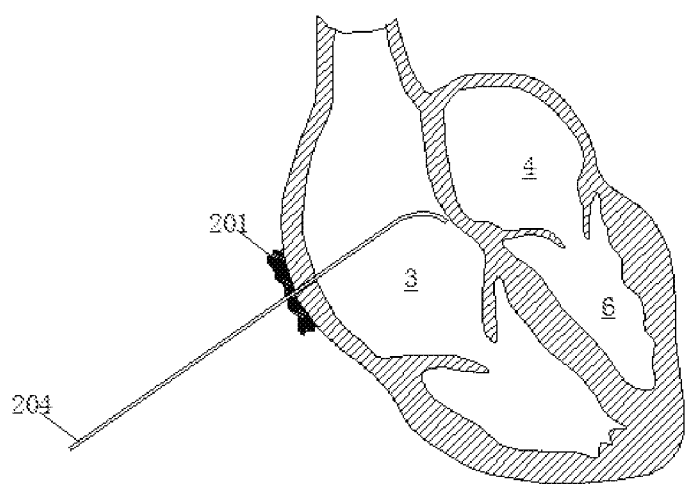

Step III, with reference to FIG. 35 and FIG. 36 together, delivering the distal end of a guide wire 204 into the right atrium 3 along an inner cavity of the puncture needle 202, removing the puncture needle 202 from the right atrium 3, and remaining the guide wire 204 in the right atrium 3.

Figure 37:
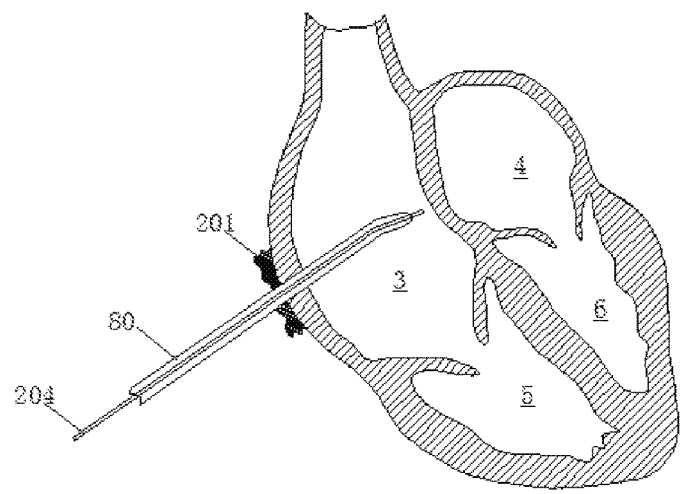
FIG. 37 is a schematic diagram of the right atrium after the distal end of a delivery sheath is delivered into the right atrium along the guide wire in FIG. 36.
Figure 38:
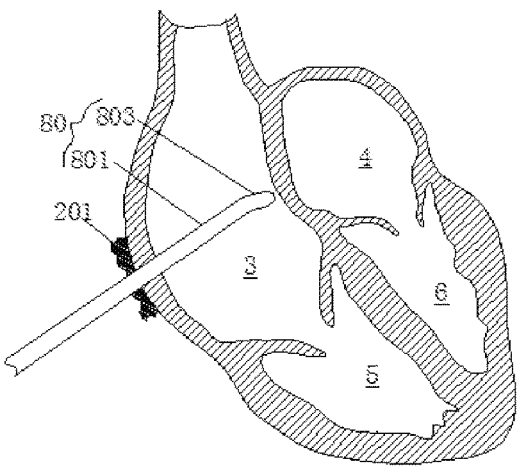
FIG. 38 is a schematic diagram of the right atrium after the guide wire in FIG. 37 is removed.

Step IV, with reference to FIG. 37 and FIG. 38, delivering a delivery sheath 80 to the right atrium 3 along the guide wire 204, removing the guide wire 204 from the right atrium 3, and remaining the delivery sheath 80 in the right atrium 3. The delivery sheath 80 includes a body section 801 and a distal end section 803 which are connected with each other; the proximal end of the distal end section 803 is connected with the distal end of the body section 801, and the distal end of the distal end section 803 extends towards the distal end of the delivery sheath 80 (namely the distal end of the distal end section 803 extends towards a direction far away from the proximal end of the body section 801). An included angle of a certain degree ranging from about 20 degrees to 30 degrees is formed between the extending direction of the distal end section 803 towards the distal end and the extending direction of the body section 801 towards the distal end, that is, the delivery sheath 80 has a certain preset angle ranging from 20 degrees to 30 degrees. In this embodiment, an included angle of about 30 degrees is formed between the extending direction of the distal end section 803 towards the distal end and the extending direction of the body section 801 towards the distal end. In other embodiments, according to an individual difference and an actual requirement of a patient, an included angle of about 20 degrees, 25 degrees or 28 degrees and the like is formed between the extending direction of the distal end section 803 towards the distal end and the extending direction of the body section 801 towards the distal end. It is because the delivery sheath 80 adopted in the implantation method of this embodiment has a preset angle, when the position of the atrial septum 31 is punctured, the puncture needle may be prevented from puncturing the posterior wall of the left atrium 4 in the surgical procedure, and the surgical risk is reduced.

Figure 39:
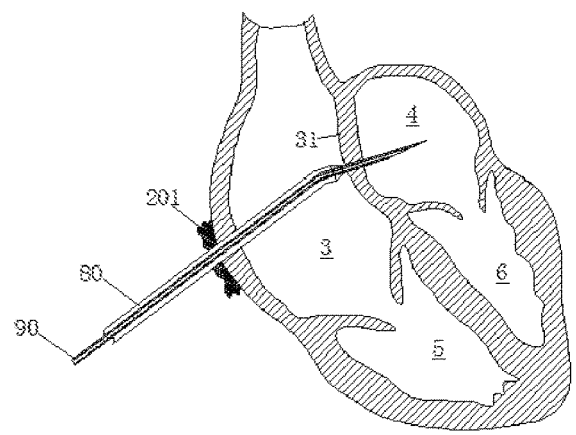
FIG. 39 is a schematic diagram of the left atrium after the distal end of a puncture needle or a radio frequency punching needle is delivered into the left atrium via the atrial septum by an inner cavity of the delivery sheath in FIG. 38.
Figure 40:
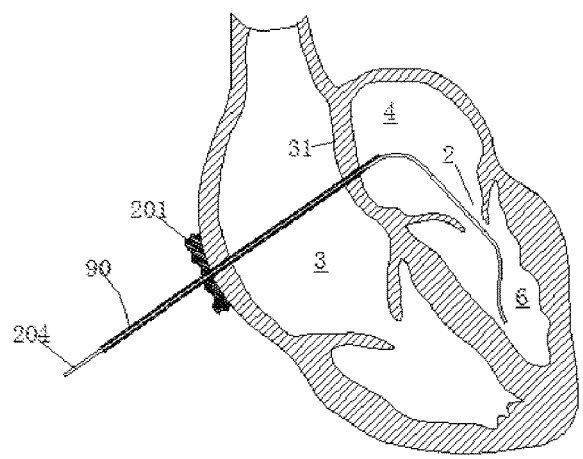
FIG. 40 is a schematic diagram of the left ventricle after the distal end of the guide wire is delivered into the left ventricle via the inner cavity of the puncture needle or the radio frequency punching needle in FIG. 39.

Step V, with reference to FIG. 39 and FIG. 40, delivering the distal end of the guide wire 204 to the left ventricle 6. Specifically, first, delivering the needle tip of the puncture needle or a radio frequency punching needle 90 to the right atrium 3 from the inside of the delivery sheath 80, and delivering the needle tip of the puncture needle or the radio frequency punching needle 90 to the left atrium 4 through the atrial septum 31 in a puncturing or punching manner; second, removing the delivery sheath 80 from the right atrium 3; then delivering the distal end of the guide wire 204 to the left atrium 4 along an inner cavity of the puncture needle or the radio frequency punching needle 90, and guiding the distal end into the left ventricle 6 through the mitral valve 2; and removing the puncture needle or the radio frequency punching needle 90 from the heart system, and remaining the distal end of the guide wire 204 in the left ventricle 6. Therefore, the distal end of the guide wire 204 is delivered to the left ventricle 6.

Further steps are the same as the steps V to XIII in the first implantation method, so that no more detailed description will be given here.

Figure 41:
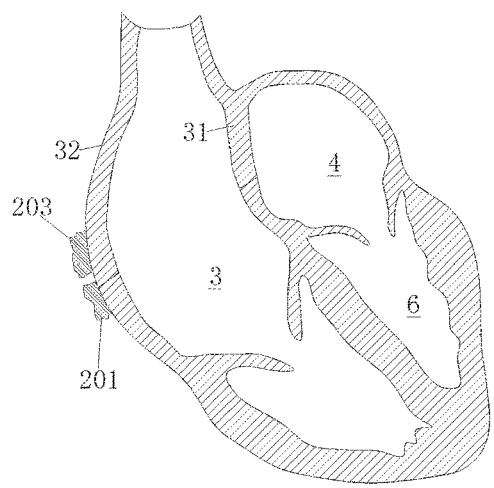
FIG. 41 is a schematic diagram of the right atrium after two pockets are disposed on the anterolateral wall of the right atrium in a third implantation method.

A third method for implanting an interventional medical device includes:

Step I, suturing two mattress type pockets 201 and 203 on the anterolateral wall 32 of the right atrium 3, specifically including: first, after a patient lies down about 40 degrees on the left, forming a small incision which is about 3 cm beside the fourth intercostal sternum of the right thorax, specifically, incising the skin, subcutaneous tissues and muscular layer fascia in sequence, and performing blunt dissection on the muscular layer until the pleural cavity; second, exposing the pericardium; then incising the pericardium and suspending the pericardium to expose the right atrium; and suturing the mattress type pockets 201 and 203 at the right atrium anterior wall 32 (as shown in FIG. 41). It should be understood that in other embodiments, according to an individual difference and an actual requirement of a patient, in order to facilitate the surgical operation, two or more small incisions may be formed in the right thorax, not limited to one small incision in this embodiment.

Figure 42:
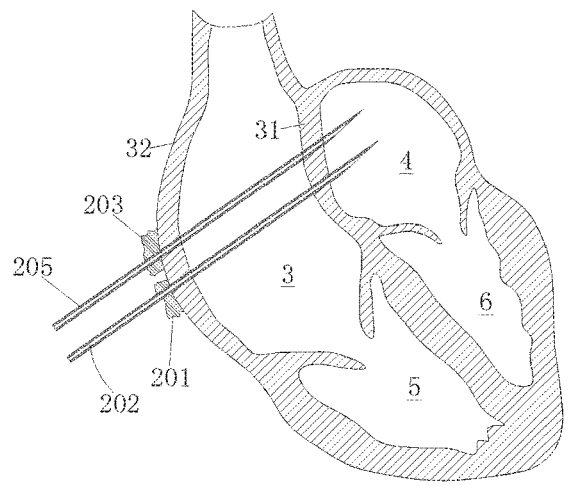
FIG. 42 is a schematic diagram of the left atrium after two puncture needles enter the left atrium respectively via the two pockets in FIG. 41.

Step II, delivering the needle tips of the puncture needles 202 and 205 into the left atrium 4 respectively, specifically, enabling the needle tips of the puncture needles 202 and 205 to puncture into the right atrium 3 from the middle portions of the mattress type pockets 201 and 203 respectively and then puncture into the atrial septum 31 to enter the left atrium 4 (as shown in FIG. 42).

Figure 43:
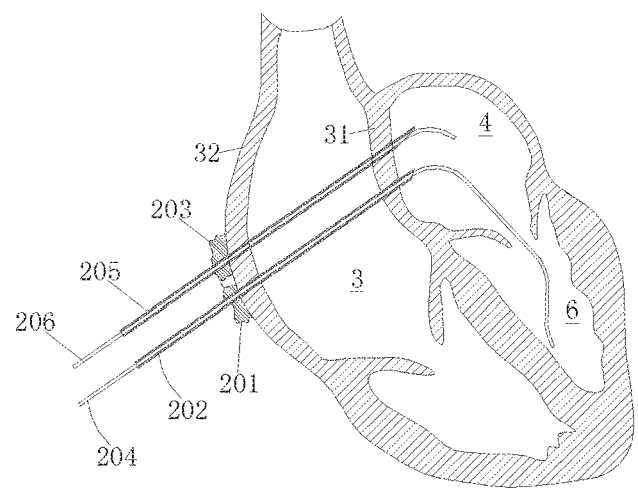
FIG. 43 is a schematic diagram of the left atrium after two guide wires enter the left atrium respectively via inner cavities of the two puncture needles in FIG. 42.

Step III, putting the distal end of the guide wire 204 into the left ventricle 6 through the right atrium 3, the atrial septum 31, the left atrium 4 and the mitral valve 2 in sequence along an inner cavity of the puncture needle 202, and putting the distal end of the guide wire 206 into the left atrium 4 through the right atrium 3 and the atrial septum 31 along an inner cavity of the puncture needle 205 (as shown in FIG. 43).

Figure 44:
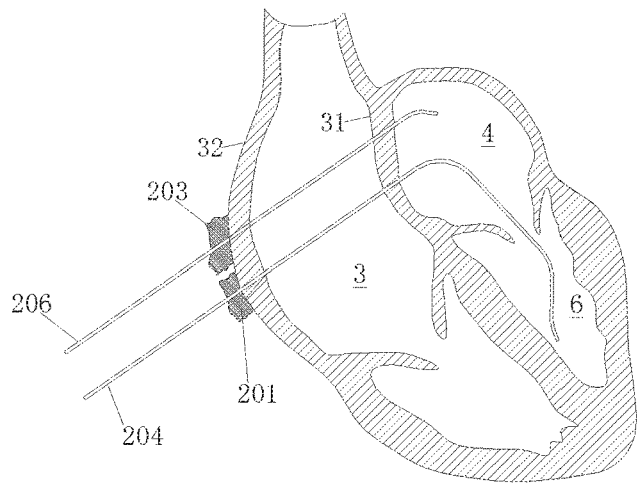
FIG. 44 is a schematic diagram of the heart system after the puncture needles are removed.
Figure 45:
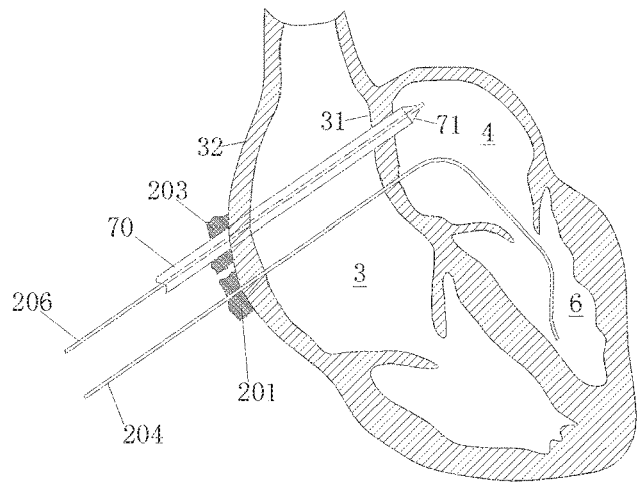
FIG. 45 is a schematic diagram of the left atrium after the distal end of a delivery sheath with an expander enters the left atrium via a guide wire.
Figure 46:
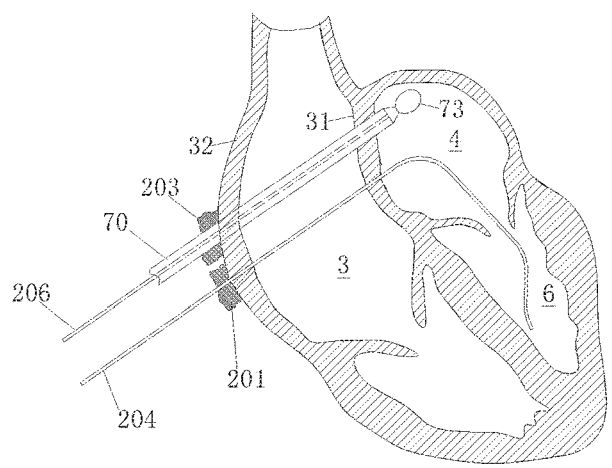
FIG. 46 is a schematic diagram of the left atrium after a surgical auxiliary device is delivered into the left atrium via a delivery sheath.

Step IV, delivering a surgical auxiliary device 73 to the left atrium 4. Specifically, first, removing the puncture needles 202 and 205 from the heart system (as shown in FIG. 44); second, delivering the distal end of a delivery sheath 70 with an expander 71 into the left atrium 4 along the guide wire 206, and tightening the mattress type pocket 203 (as shown in FIG. 45); then removing the guide wire 206 and the expander 71 from the heart system; and then, delivering the surgical auxiliary device 73 into the left atrium 4 through the delivery sheath 70 to assist the surgery (as shown in FIG. 46). In this embodiment, the surgical auxiliary device 73 is an ultrasonic probe. In other embodiments, the surgical auxiliary device 73 also may be a surgical robot.

Figure 47:
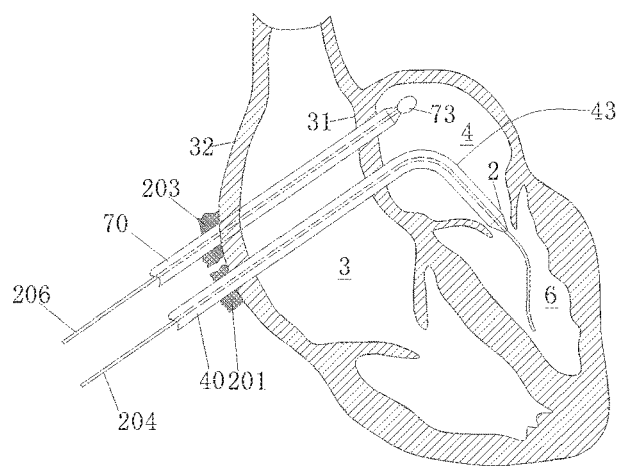
FIG. 47 is a schematic diagram of the mitral valve after the distal end of an interventional medical device-loaded delivery device reaches the mitral valve via the other guide wire.

Step V, delivering the distal end of a delivery device 40 with a valve device 50 to the left ventricle 6 along the guide wire 204, tightening the mattress type pocket 201, and adjusting the external sheath 43 under the auxiliary action of the surgical auxiliary device 73 to enable the angle of the distal end of the sheath 43 to be perpendicular to a plane where the mitral valve 2 is placed (as shown in FIG. 47).

It should be understood that in other embodiments, the third implantation method may further include a step, which is like the step of measuring the size of the mitral annulus 8 to assist in selecting the interventional medical device 50 in the first implantation method, between the fourth step and the fifth step.

It should be understood that in other embodiments, for example when the surgical auxiliary device 73 is the ultrasonic probe, the fourth step and the fifth step of delivering the distal end of the delivery device 40 with the valve device 50 to the left ventricle 6 along the guide wire 204 may be carried out at the same time under the condition that during adjustment of the angle of the distal end of the external sheath 43, the surgical auxiliary device 73 has been delivered to the left atrium 4 and may assist in adjusting the external sheath 43. It should be further understood that in other embodiments, when the surgical auxiliary device 73 is the ultrasonic probe, the fifth step of delivering the distal end of the delivery device 40 with the valve device 50 to the left ventricle 6 along the guide wire 204 also may be carried out before the fourth step under the condition that during adjustment of the angle of the distal end of the external sheath 43, the surgical auxiliary device 73 has been delivered to the left atrium 4 and may assist in adjusting the external sheath 43.

The steps from VI to XII are the same as those in the first implantation method, so that no more detailed description will be given here.

Figure 48:
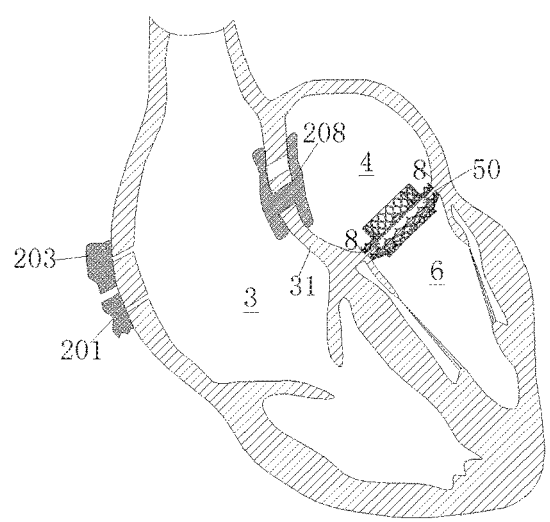
FIG. 48 is a schematic diagram of disposal of an occluder for occluding two puncture holes of the atrial septum and ligation of two pockets.

Step XIII, checking whether there is residual shunt at the punctured portion of the atrial septum 31 through ultrasonic imaging; if the residual shunt is obvious or clearly visual, carrying out atrial septum occlusion, that is, implanting an occluder 208 under the guide of the guide wire 204 to occlude the punctured portion of the atrial septum 31 (as shown in FIG. 48); and if there is no residual shunt, removing the delivery device 40, the delivery sheath 70 and the surgical auxiliary device 73 from the heart system, ligating the pockets 201 and 203, and suturing the small incision in the right thorax, thus completing the whole surgical procedure.

It should be understood that when the external sheath 43 of the delivery device 40 has two inner cavities which are used to deliver the interventional medical device and the surgical auxiliary device respectively, the above-mentioned two puncture channels also may be replaced by one puncture channe.

Figure 49:
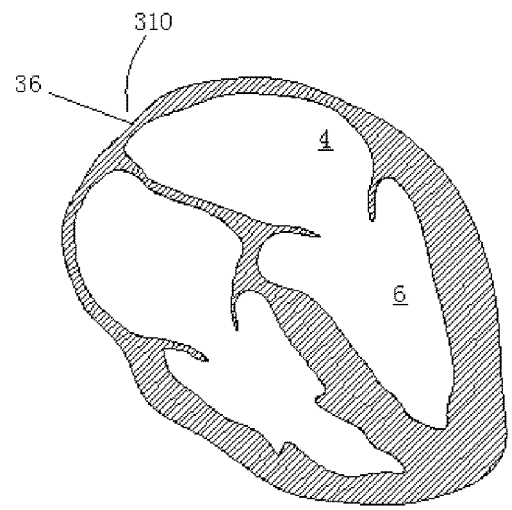
FIG. 49 is a schematic diagram of a pre-puncture position on the interatrial groove in a fourth implantation method.
Figure 50:
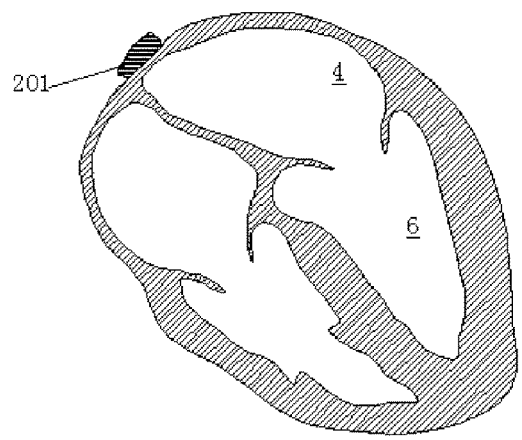
FIG. 50 is a schematic diagram of a pocket disposed around the pre-puncture position in FIG. 49.

The invention further provides a fourth method for implanting an interventional medical device 50. Under the assistance of a thoracoscope, the method includes:

Step I, with reference to FIG. 49 and FIG. 50 together, suturing a mattress type pocket 201 at a pre-puncture position 36 of the interatrial groove, including: first, forming a small incision which is about 2.5 cm in the fourth intercostal of the anterior axillary line of the right anterior thorax, specifically, incising the skin, subcutaneous tissues and muscular layer fascia in sequence, and performing blunt dissection on the muscular layer until the pleural cavity; second, exposing the pericardium; then incising the pericardium and suspending the pericardium to expose the interatrial groove 310; and determining the pre-puncture position 36 under the guide of the thoracoscope, and suturing the mattress type pocket 201 around the pre-puncture position 36.

Figure 51:
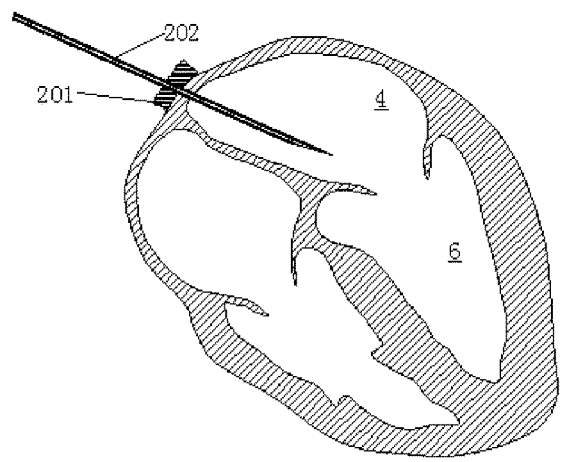
FIG. 51 is a schematic diagram of the left atrium after a puncture needle enters the left atrium via the pocket in FIG. 50.

Step II, with reference to FIG. 51, enabling the needle tip of a puncture needle 202 to puncture the interatrial groove 310 from the middle portion of the mattress type pocket 201 to enter the left atrium 4.

The steps from III to XI are substantially the same as those in the first implantation method, so that no more detailed description will be given.

Figure 52:
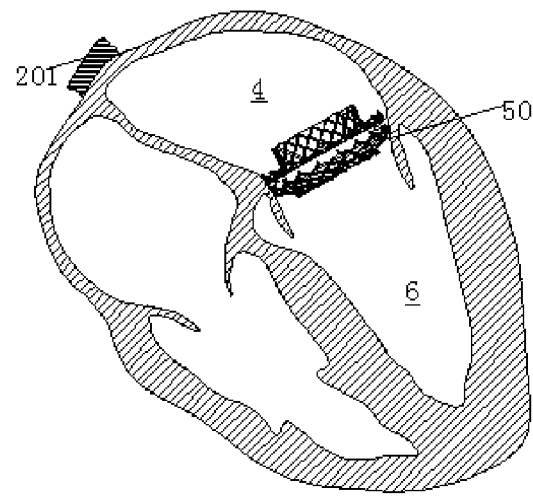
FIG. 52 is a schematic diagram of an interventional medical device that is implanted via the interatrial groove.

Step XII, with reference to FIG. 52, removing all the devices other than the interventional medical device 50 from the body of a patient, ligating the pocket 201, and suturing the small incision in the right thorax, thus completing the whole surgical procedure.

In the process of the fourth implantation method of the interventional medical device 50, no extracorporeal circulation is needed, so that the harm of a large surgical trauma is avoided. Puncturing is implemented via the small incision in the right thorax instead of a vascular path, so that the size of a blood vessel may not limit the size of the interventional medical device, and the structural design of the interventional medical device is flexible; the puncturing is carried out via the interatrial groove which has the blood pressure less than that of the left ventricle, so that no bleeding or a small bleeding amount is caused at a puncture point, and the puncturing is easy to carry out; an interventional medical device recycling device is arranged in the left atrium to avoid incidence of left ventricular outflow tract obstruction; the delivery device for carrying the interventional medical device is relatively far from the chordae tendineaem, so that the delivery device or the interventional medical device may hardly touch the chordae tendineae, thus reducing the possibility that the chordae tendineae twines around the delivery device or the interventional medical device, and making the operation process simpler.

It should be understood that in other embodiments, the mattress type pocket also may be sutured on the left atrial wall, and the needle tip of the puncture needle also may puncture into the left atrium through the mattress type pocket on the left atrial wall; in that case, after the needle tip of the puncture needle enters the left atrium, other steps of the implantation method also may adopt the steps from III to XII in the fourth implantation method. It should be also understood that the implantation method of the present application may be used to implant an artificial mitral valve, and may complete tricuspid valve replacement, mitral annulus repairing, left atrial appendage occlusion, defibrillation and the like after being slightly changed.

Figure 53:
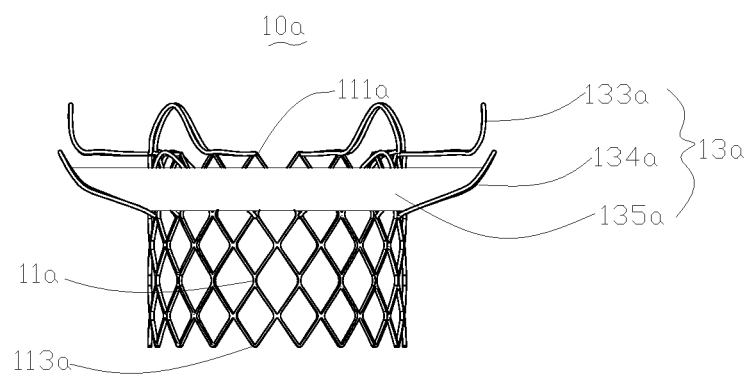
FIG. 53 is a schematic diagram of a stent of an interventional medical device provided by another embodiment of the present application.

With reference to FIG. 53, another embodiment of the present application provides an artificial heart valve stent 10*a*, including a tubular stent body 11*a*, an inflow side skirt 133*a* disposed on the external wall of the stent body 11*a*, an outflow side skirt 134*a* disposed on the external wall of the stent body 11*a*, and flow resisting cloth 135*a* disposed on the outflow side skirt 134*a*. The free ends of the inflow side skirt 133*a* and the outflow side skirt 134*a* both extend towards an inflow side end 111*a* of the stent body 11*a*; and the inflow side skirt 133*a* is used for cooperating with the outflow side skirt 134*a* to clamp artificial heart valve tissues. The distance between the end, which is connected with the stent body 11*a*, of the inflow side skirt 134*a* and the end, which is connected with the stent body 11*a*, of the outflow side skirt 134*a* ranges from 2 mm to 6 mm. In this embodiment, the inflow side skirt 133*a* and the outflow side skirt 134*a* are both arranged on the stent body 11*a* in a weaving manner, and the flow resisting cloth 135*a* is only arranged on the outflow side skirt 134*a*; and the distance between the end, which is connected with the stent body 11*a*, of the inflow side skirt 134*a* and the end, which is connected with the stent body 11*a*, of the outflow side skirt 134*a* is 2 m.

Figure 54:
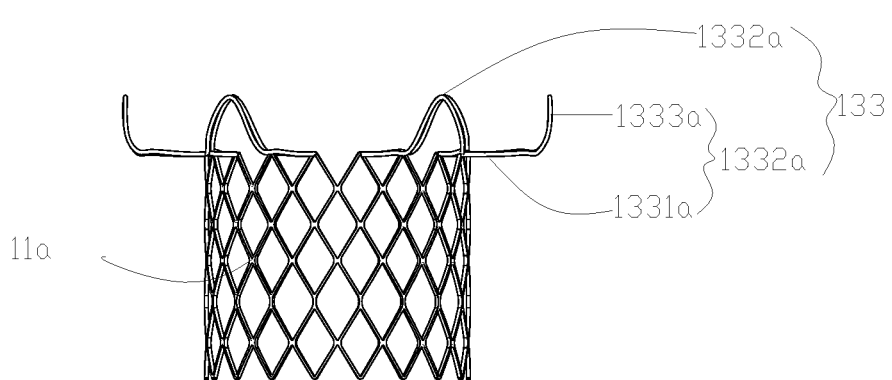
FIG. 54 is a schematic diagram of the stent in FIG. 53 after an outflow side skirt and a flow resisting cloth of the stent are removed.
Figure 55:
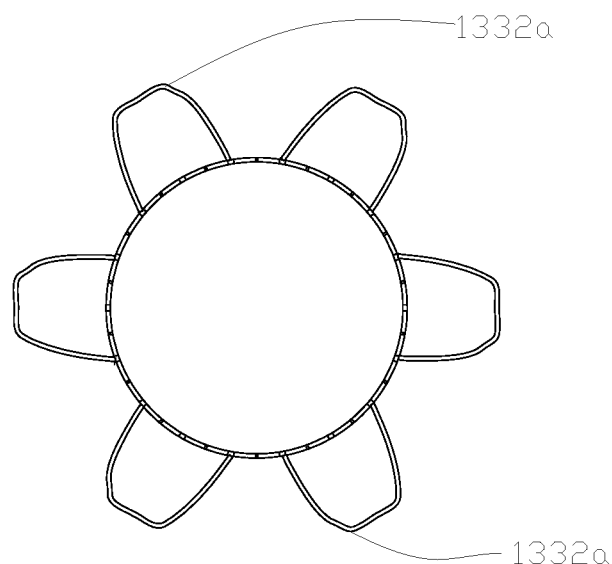
FIG. 55 is a top view of the stent of FIG. 54.

With reference to FIG. 54 and FIG. 55 together, the inflow side skirt 133*a* is arranged at the inflow side end 111*a* of the stent body 11*a*, and includes multiple mutually separated first skirt subunits 1332*a*. Each first skirt subunit 1332 *a* is formed by weaving a nickel-titanium wire and shaping the woven wire, and is arranged on the stent body 11 *a* in a weaving manner. Each first skirt subunit 1332*a* includes an inflow side clamping portion subunit 1331*a* and an inflow side upwarping portion subunit 1333*a*. The inflow side clamping portion subunits 1331*a* are located between the inflow side upwarping portion subunits 1333*a* and the stent body 11*a*. Each inflow side clamping portion subunits 1331*a* are substantially parallel to the cross section, which is perpendicular to the longitudinal central line of the stent body 11*a*. Each inflow side upwarping portion subunit 1333*a* is substantially parallel to the longitudinal central line of the stent body 11 *a*. The multiple inflow side clamping portion subunits 1331*a* jointly form an inflow side clamping portion of the inflow side skirt 133*a*; and the multiple inflow side upwarping portion subunits 1333*a* jointly form an inflow side upwarping portion of the inflow side skirt 133*a*.

Figure 56:
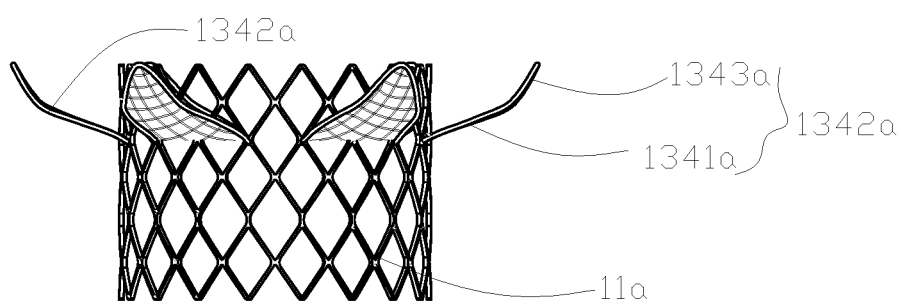
FIG. 56 is a schematic diagram of the stent in FIG. 53 after an inflow side skirt and the flow resisting cloth of the stent are removed.
Figure 57:
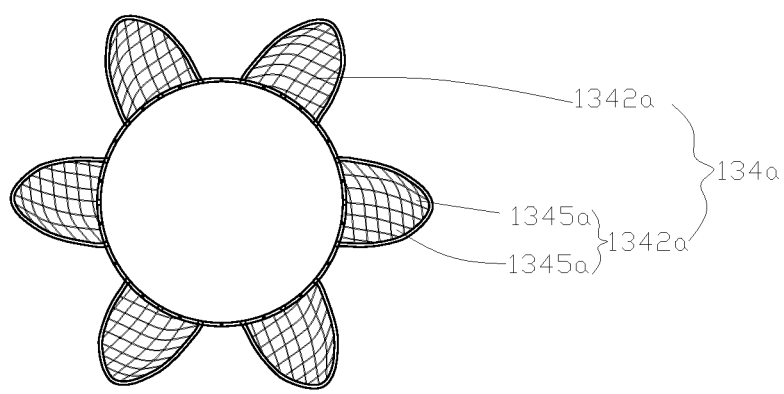
FIG. 57 is a top view of FIG. 56.

With reference to FIG. 56 and FIG. 57 together, the outflow side skirt 134*a* includes multiple mutually separated second skirt subunits 1342*a*. In this embodiment, the number of the second skirt subunits 1342*a* is equal to that of the first skirt subunits 1332*a*, and the multiple second skirt subunits 1342*a* each correspond to the first skirt subunits 1332*a*.

Each second skirt subunit 1342*a* is formed by weaving a nickel-titanium wire and shaping the woven wire, and is arranged on the stent body 11*a* in a weaving manner. Each second skirt subunit 1342*a* includes an outflow side clamping portion subunit 1341*a* and an outflow side upwarping portion subunit 1343*a*. The outflow side clamping portion subunits 1341*a* are located between the outflow side upwarping portion subunits 1343*a* and the stent body 11*a*. An included angle is formed between each outflow side clamping portion subunit 1341*a* and the longitudinal central line of the stent body 11*a*.

In this embodiment, the included angle between each outflow side clamping portion subunit 1341*a* and the longitudinal central line of the stent body 11*a* is 50 degrees; and the distance between each outflow side clamping portion subunit 1341*a* and each corresponding inflow side clamping portion subunit 1331*a* along the longitudinal central axial line of the stent body 11*a* is gradually reduced outwards from the stent body 11*a*. Each outflow side upwarping portion subunit 1343*a* is substantially parallel to the longitudinal central line of the stent body 11*a*. The multiple outflow side clamping portion subunits 1341*a* jointly form an outflow side clamping portion of the outflow side skirt 134*a*; and the multiple outflow side upwarping portion subunits 1343*a* jointly form an outflow side upwarping portion of the outflow side skirt 134*a*. Each second skirt subunit 1342*a* also includes a grid 1345*a* formed by crossing multiple weaving wires so as to better arrange the flow resisting cloth 135*a*.

It should be understood that outflow side anchoring members also may be arranged on grid lines of the grid 1345*a*.

It should be understood that at least one second skirt subunit 1342*a* in the outflow side skirt 134*a* also may be arranged on the stent body 11*a* by welding. It should be further understood that the outflow side skirt 134*a* may be replaced by the outflow side skirt 134 in the first embodiment. It should be further understood that the inflow side skirt 133*a* may be replaced by the inflow side skirt 133 in the first embodiment.

It should be understood that although intervention of the implantation method according to the present application does not occur via blood vessel, cardiac apex or other ways, according to an individual difference and an actual condition of a patient, interventional medical devices which are implanted via blood vessels or cardiac apexes or other ways, and have the same structure as that of the interventional medical device 50 of the present application still fall within the scope of protection of the interventional medical device claimed by the present application.

All technical features of the above-mentioned embodiments may be combined, as desired. In order to make the description concise, not all possible combinations of all the technical features in the above-mentioned embodiments are described, but if only the combinations of these technical features have no contradictions, they shall all be deemed to fall within the scope of the described.

The above-mentioned embodiments only express several implementation modes of the present application, and their descriptions are relatively specific and particular, but not intended to limit the scope of the invention patent. It should be noted that a person of ordinary skill in the art can further make a variety of deformations and improvements without departing from the concept of the present application, and these deformations and improvements shall all fall within the protection scope of the present application. Therefore, the protection scope of the invention patent shall be based on attached claims.

The invention claimed is:

1. An artificial heart valve stent, comprising:
a tubular stent body having an inflow side end and an outflow side end opposite to the inflow side;
an inflow side skirt surrounding the external wall of the stent body; and
an outflow side skirt surrounding and disposed on the external wall of the stent body, wherein the outflow side skirt is configured between the outflow side end of the stent body and the inflow side skirt; and
a tubular connection stent having two ends and an external wall and surrounding the external wall of the stent body, the inflow side skirt and the outflow side skirt being located at the two ends of the tubular connection stent, respectively,
wherein the inflow side skirt, the outflow side skirt, and the tubular connection stent are integrally formed in manner by which the inflow side skirt and the outflow side skirt extend outwards from the external wall of the tubular connection stent, and the inflow side skirt and the outflow side skirt are fixedly connected to the stent body via the tubular connection stent before being implanted;
wherein in a released state, free ends of both the inflow side skirt and the outflow side skirt extend towards the inflow side end, and
the inflow side skirt is configured for cooperating with the outflow side skirt to clamp heart valve tissues.

2. The artificial heart valve stent according to claim 1, wherein the tubular connection stent and the stent body are independently formed, and then are fixedly connected into a whole.

3. The artificial heart valve stent according to claim 1, wherein an end of the inflow side skirt, which is connected with the tubular connection stent, comprises a projection that extends from a plane on the inflow side skirt that is parallel to the longitudinal central axial line of the tubular connection stent, the inflow side end of the tubular connection stent comprises a projection that extends from a plane parallel to the longitudinal central axial line of the tubular connection stent, and the projection from the end of the inflow side skirt and the projection from the inflow side end are separated.

4. The artificial heart valve stent according to claim 3, wherein a distance between the end of the inflow side skirt, which is connected with the tubular connection stent, and the inflow side end is greater than or equal to a distance between an end of the outflow side skirt, which is connected with the tubular connection stent, and the outflow side end.

5. The artificial heart valve stent according to claim 3, wherein an end of the outflow side skirt, which is connected with the tubular connection stent, comprises a projection that extends from a plane parallel to the longitudinal central axial line of the tubular connection stent, the outflow side end comprises a projection that extends from a plane parallel to the longitudinal central axial line of the tubular connection stent, and the projection from the end of the outflow side skirt and the projection from the outflow side end are separated.

6. The artificial heart valve stent according to claim 1, wherein the inflow side skirt extends away from the external wall of the tubular connection stent, and comprises an inflow side clamping portion connected with and surrounding the tubular connection stent, and an inflow side upwarping portion connected with the inflow side clamping portion; the inflow side clamping portion is located between the inflow side upwarping portion and the tubular connection stent; the inflow side upwarping portion having an end, which is away from the inflow side clamping portion, that corresponds with a free end of the inflow side skirt; and an included angle is formed between the inflow side upwarping portion and the inflow side clamping portion.

7. The artificial heart valve stent according to claim 6, wherein the inflow side upwarping portion comprises an inflow side waveform structure surrounding the tubular connection stent.

8. The artificial heart valve stent according to claim 6, wherein the outflow side skirt extends away from the external wall of the tubular connection stent, and comprises an outflow side clamping portion connected with and surrounding the tubular connection stent, and an outflow side upwarping portion connected with the outflow side clamping portion; the outflow side clamping portion is located between the outflow side upwarping portion and the tubular connection stent; an end of the outflow side upwarping portion, which is away from the outflow side clamping portion, corresponds to a free end of the outflow side skirt; and an included angle is formed between the outflow side upwarping portion and the outflow side clamping portion.

9. The artificial heart valve stent according to claim 1, wherein the inflow side skirt comprises a plurality of mutually separated first skirt subunits, and each first skirt subunit is disposed on the tubular connection stent in a weaving manner.

10. The artificial heart valve stent according to claim 1, wherein the valve stent further comprises a plurality of inflow side anchoring members arranged on the inflow side skirt, and the inflow side anchoring members on the inflow side skirt have free ends that extend towards the outflow side end.

11. The artificial heart valve stent according to claim 1, wherein a distance between the end, which is connected with the tubular connection stent, of the inflow side skirt and the end, which is connected with the tubular connection stent, of the outflow side skirt ranges from 2 mm to 6 mm.

12. The artificial heart valve stent according to claim 1, wherein the valve stent further comprises a plurality of connection elements arranged on the free end of the inflow side skirt.

13. The artificial heart valve stent according to claim 1, wherein the valve stent further comprises a flow resisting cloth covering at least one of the inflow side skirt and the outflow side skirt.

14. The artificial heart valve stent according to claim 1, further comprising valve leaflets, wherein the valve leaflets are arranged inside the tubular connection stent.

15. An implantation method of an interventional medical device, comprising:
    forming a small incision in the right thorax to expose the atrium;
    delivering the artificial heart valve according to claim 14 to an implantation position of a heart system through the small incision; and
    fixing the artificial heart valve on tissues of the heart system.

16. The implantation method according to claim 15, wherein the heart valve is an artificial mitral valve; and, further comprising, after the step of forming the small incision in the right thorax to expose the atrium, and before the step of delivering the heart valve to the implantation position of the heart system through the small incision, delivering a guide wire to the left ventricle through the small incision.

17. The implantation method according to claim 16, wherein the step of delivering the guide wire to the left ventricle through the small incision comprises: suturing a mattress type pocket on the atrial wall, delivering the needle tip of a puncture needle into the left atrium through the mattress type pocket, then delivering the distal end of the guide wire into the left atrium along an inner cavity of the puncture needle, and delivering the distal end into the left ventricle through the mitral valve.

18. The implantation method according to claim 17, wherein the step of delivering the guide wire to the left ventricle through the small incision comprises: suturing a mattress type pocket on the right atrial wall, delivering the needle tip of a radio frequency punching needle into the left atrium through the mattress type pocket, the right atrium and the atrial septum, then delivering the distal end of the guide wire into the left atrium along an inner cavity of the radio frequency punching needle, and delivering the distal end into the left ventricle through the mitral valve.

19. The implantation method according to claim 16, wherein the step of delivering the guide wire to the left ventricle through the small incision comprises: suturing a mattress type pocket around a pre-puncture position of the interatrial groove, delivering the needle tip of a puncture needle into the left atrium through the mattress type pocket, then delivering the distal end of the guide wire into the left atrium along an inner cavity of the puncture needle, and delivering the distal end into the left ventricle through the mitral valve.

\* \* \* \* \*